(12) United States Patent
Perkins et al.

(10) Patent No.: US 11,155,836 B2
(45) Date of Patent: Oct. 26, 2021

(54) COMPOSITIONS AND METHODS FOR MONITORING IN REAL-TIME CONSTRUCTION AND BIOENGINEERING OF MAMMALIAN SYNTHETIC CHROMOSOMES

(71) Applicant: SynPloid Biotek, LLC, Savannah, GA (US)

(72) Inventors: Edward Perkins, Savannah, GA (US); Amy Greene, Savannah, GA (US)

(73) Assignee: CarryGenes Bioengineering, Savannah, GA (US)

( * ) Notice: Subject to any disclaimer, the term of this patent is extended or adjusted under 35 U.S.C. 154(b) by 704 days.

(21) Appl. No.: 15/548,236

(22) PCT Filed: Feb. 9, 2016

(86) PCT No.: PCT/US2016/017179
§ 371 (c)(1),
(2) Date: Aug. 2, 2017

(87) PCT Pub. No.: WO2016/130568
PCT Pub. Date: Aug. 18, 2016

(65) Prior Publication Data
US 2018/0010150 A1      Jan. 11, 2018

Related U.S. Application Data

(60) Provisional application No. 62/113,707, filed on Feb. 9, 2015.

(51) Int. Cl.
*C12N 15/90* (2006.01)
*C12N 15/63* (2006.01)

(52) U.S. Cl.
CPC ............ *C12N 15/90* (2013.01); *C12N 15/63* (2013.01); *C07K 2319/60* (2013.01); *C12N 2800/208* (2013.01)

(58) Field of Classification Search
None
See application file for complete search history.

(56) References Cited

U.S. PATENT DOCUMENTS

| 6,348,353 B1 * | 2/2002 | Harrington ............ C12N 15/66 435/320.1 |
| 2002/0160410 A1 | 10/2002 | Hadlaczky et al. |
| 2004/0096891 A1 | 5/2004 | Bennett |
| 2005/0181506 A1 | 8/2005 | Perkins et al. |
| 2007/0004002 A1 | 1/2007 | Okazaki |
| 2008/0299592 A1 | 12/2008 | Miller |
| 2011/0318832 A1 | 12/2011 | Cech et al. |
| 2012/0064578 A1 | 3/2012 | Perkins et al. |
| 2012/0093785 A1 | 4/2012 | Oshimura et al. |
| 2014/0295501 A1 | 10/2014 | Katona et al. |
| 2018/0010150 A1 | 1/2018 | Perkins et al. |

FOREIGN PATENT DOCUMENTS

| EP | 2218786 A4 | 6/2011 |
| EP | 2218786 B1 | 9/2013 |
| EP | 2522725 B1 | 10/2016 |
| EP | 1559782 B1 | 12/2016 |
| WO | 97/40183 A1 | 4/2000 |
| WO | 0018941 A1 | 4/2000 |

OTHER PUBLICATIONS

Kazuki et al., Molecular Therapy, vol. 19, No. 9, 1591-1601 (Year: 2011).*
Kouprina, et al., "A new generation of human artificial chromosomes for functional genomics and gene therapy", Cell Mol. Life Sci, 70(7):1135-48 (2013).
International Search Report for PCT/US2016/017179, dated Aug. 15, 2017, all pages.
International Preliminary Report on Patentability, dated Aug. 24, 2017 by the International Bureau of WIPO for International Application No. PCT/US2016/017179, filed Feb. 9, 2016.
Basu, J., "Artificial and Engineered Chromosomes: Non-Integrating Vectors for Gene Therapy." Trends in Molecular Medicine, Elsevier Current Trends, vol. 11 (5), pp. 251-258 (2005).
Ikeno, M et al., "Construction of YAC-based mammalian artificial chromosomes", Nature Biotechnology, (May 1998), vol. 16, No. 5, pp. 431-439, XP009060040.
Kazuki, et al., "Refined human artificial chromosome vectors for gene therapy and animal transgenesis." Gene Therapy, vol. 18(4):384-393 (2010).
Kazuki, Y et al., "Human Artificial Chromosomes for Gene Delivery and the Development of Animal Models", Molecular Therapy, (2011) 19(9):1591-1601. doi:10.1038/mt.2011.136, XP055581607.
Kouprina, et al., (2014) "Human Artificial Chromosome-Based Gene Delivery Vectors for Biomedicine and Biotechnology." Expert Opinion on Drug Delivery. 11(4):517-535.
Kurosaki, et al., "Integration-free and stable expression of FVIII using a human artificial chromosome." Journal of Human Genetics, vol. 56 (10), pp. 727-733 (2011).
Martella, et al., "Mammalian Synthetic Biology: Time for Big MACs." ACS Synthetic Biology, vol. 5 (10), pp. 1040-1049 (2016).
Ren, X et al., "A Novel Human Artificial Chromosome Vector Provides Effective Cell Lineage-Specific Transgene Expression in Human Mesenchymal Stem Cells", Stem Cells, (Nov. 1, 2005), vol. 23, No. 10, doi:10.1634/stemcells.2005-0021, pp. 1608-1616, XP055473399.
Shitara, et al., 2008, "Telomerase-mediated life-span extension of human primary fibroblasts by human artificial chromosome (HAC) vector." Biochem. Biophys. Res. Commun. 369(3):807-11.
Suzuki, et al., (2014), "A Novel System for Simultaneous or Sequential Integration of Multiple Gene-Loading Vectors into a Defined Site of a Human Artificial Chromosome." Plos One. 9(10), pp. 1-9 (2014).

(Continued)

*Primary Examiner* — Nancy J Leith
(74) *Attorney, Agent, or Firm* — Susan Myers Fitch

(57) ABSTRACT

The present invention encompasses compositions and methods to allow one to monitor formation of synthetic chromosomes in real-time via standardized fluorescent technology, eliminating the need for cumbersome, expensive, and possibly mutagenic analysis.

21 Claims, 10 Drawing Sheets

(56) References Cited

OTHER PUBLICATIONS

Takiguchi, et al., "A Novel and Stable Mouse Artificial Chromosome Vector," ACS Synthetic Biology, vol. 3 (12), pp. 903-914 (2014).

Toth, et al., "Novel Method to Load Multiple Genes onto a Mammalian Artificial Chromosome." Plos One, Public Library of Science, US, vol. 9 (1), pp. e85565-1 (2014).

Vanderbyl, S et al., "Transfer and Stable Transgene Expression of a Mammalian Artificial Chromosome into Bone Marrow-Derived Human Mesenchymal Stem Cells", Stem Cells, (May 2004), vol. 22, No. 3, doi:doi:10.1634/stemcells.22-3-324, pp. 324-333, XP002506658.

Yamaguchi, et al., 2011 "A Method for Producing Transgenic Cells Using a Multi-Integrase System on a Human Artificial Chromosome Vector." PLoS ONE 6(2): e17267. https://doi.org/10.1371/journal.pone.0017267.

Lindenbaum et al., "A mammalian artificial chromosome engineering system (ACE System) applicable to biopharmaceutical protein production, transgenesis and gene-based cell therapy," Nucleic Acids Research, (2004), vol. 32, No. 21, pp. 1-15 (p. e172, XP002741726).

European Search Report dated Apr. 29, 2019 by the European Patent Office in EP Patent Application No. 16749728.8, filed Feb. 9, 2016 based on PCT/US2016/017179.

Extended European Search Report dated May 24, 2018 by the European Patent Office in EP Patent Application No. 16749728.8, filed Feb. 9, 2016 based on PCT/US2016/017179.

Lindenbaum et al., "A mammalian artificial chromosome engineering system (ACE System) applicable to biopharmaceutical protein production, transgenesis and gene-based cell therapy," Nucleic Acids Research, (2004), vol. 32, No. 21, p. e172, XP002741726.

Rocchi et al., "*Escherichia coli*-Cloned CFTR Loci Relevant for Human Artificial Chromosome Therapy," Human Gene Therapy (2010) 21:1077-1092.

Kanda et al., "Histone-GFP fusion protein enables sensitive analysis of chromosome dynamics in living mammalian cells," Current Biology, (1998), vol. 8, No. 7, pp. 377-385.

Scheer et al., "Generation and utility of genetically humanized mouse models." Drug Discovery Today, (2013), vol. 18, Nos. 23/24, pp. 1200-1211.

Katoh et al., "Construction of a novel human artificial chromosome vector for gene delivery," Biochemical and Biophysical Research Communications, (2004), vol. 321, pp. 280-290.

Purschke et al., "Phototoxicity of Hoechst 33342 in time-lapse fluorescence microscopy," Photochemical & Photobiological Sciences, (2010), vol. 9, pp. 1634-1639.

* cited by examiner

COMPOSITIONS AND METHODS FOR MONITORING IN REAL-TIME CONSTRUCTION AND BIOENGINEERING OF MAMMALIAN SYNTHETIC CHROMOSOMES

CROSS REFERENCE TO RELATED APPLICATIONS

The present application is a U.S. 371 National Phase filing of International PCT Patent Application No. PCT/US16/17179, filed Feb. 9, 2016, which claims the benefit of U.S. Priority Patent Application No. 62/113,707, filed Feb. 9, 2015, both incorporated herein by reference.

STATEMENT REGARDING GOVERNMENT SUPPORT

This invention was made with Government support under contract D15PC00008 awarded by DARPA. The Government has certain rights in this invention.

FIELD OF THE INVENTION

The field of the invention encompasses compositions and methods to allow one to monitor production of synthetic chromosomes in real-time via standardized microscopy.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The ability to generate fully-functional mammalian synthetic chromosomes represents a powerful system for cell-based correction of genetic disorders, production of recombinant proteins in transgenic animals, analysis of regulation and expression of large human genes in a variety of cell types as well as in animal models of human disease, studies of meiosis and chromosome structure, directing cell differentiation and dedifferentiation, formation of induced pluripotent stem cells, creation of novel autocrine and paracrine cellular communication networks, creation of multi-expression systems capable of stoichiometric production of multiple encoded factors, production of biological circuits, insertion of DNA elements capable of probing the nuclear architecture and downstream uses for regulating genomic expression using discovered interactions in the nuclear architecture, and manipulation of large DNA elements such as but not limited to chromosome arm exchange onto the synthetic chromosome or incorporation of multiple large DNA elements onto the synthetic chromosome.

Fully-functional mammalian synthetic chromosomes offer several advantages over viral-based delivery systems including increased payload size, the fact that extrachromosomal maintenance avoids potential host-cell disruption, avoidance of transcriptional silencing of introduced genes and possible immunological complications, and mammalian synthetic chromosomes can be derived from and tailored to the species into which the synthetic chromosome is to be inserted. However, while successful production of mammalian synthetic chromosomes has been demonstrated, confirmation of successful chromosome production requires extensive screening time and effort to identify and characterize synthetic chromosomes of interest. The synthetic chromosome production process, is, in effect, blind. Thus, there is a need in the art for compositions and methods that allow one to track production of new synthetic chromosomes in real-time while they are being generated. The present invention provides methods and compositions that address this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description, including those aspects illustrated in the accompanying drawings and defined in the appended claims.

In some embodiments, the present invention provides a method for screening production of synthetic chromosomes comprising: constructing a synthetic chromosome production reporter cell line comprising an endogenous chromosome tag and a synthetic chromosome tag, wherein the endogenous chromosome tag and synthetic chromosome tag become stably integrated into the synthetic chromosome production reporter cell line genome; transfecting the synthetic chromosome production reporter cell line with synthetic chromosome production components; and monitoring production of the synthetic chromosome in the synthetic chromosome production reporter cell line.

In yet other embodiments, the present invention provides a method for screening production of synthetic chromosomes comprising: providing a synthetic chromosome production reporter cell line; transfecting the synthetic chromosome production reporter cell line with synthetic chromosome production components and an endogenous chromosome tag and a synthetic chromosome tag, wherein the endogenous chromosome tag and synthetic chromosome tag become stably integrated into the synthetic chromosome; and monitoring production of the synthetic chromosome in the synthetic chromosome production reporter cell line.

In still other embodiments, the present invention provides a method for screening production of synthetic chromosomes comprising: constructing a synthetic chromosome production reporter cell line comprising an endogenous chromosome tag, wherein the endogenous chromosome tag becomes stably integrated into the synthetic chromosome production reporter cell line genome; transfecting the synthetic chromosome production reporter cell line with synthetic chromosome production components and a synthetic chromosome tag, wherein the synthetic chromosome tag becomes stably integrated into the synthetic chromosome; and monitoring production of the synthetic chromosome in the synthetic chromosome production reporter cell line.

In yet other embodiments, the present invention provides a method for screening production of synthetic chromosomes comprising: constructing a synthetic chromosome production reporter cell line comprising a synthetic chromosome tag, wherein the synthetic chromosome tag becomes stably integrated into the synthetic chromosome production reporter cell line genome; transfecting the synthetic chromosome production reporter cell line with synthetic chromosome production components and an endogenous chromosome tag, wherein the endogenous chromosome tag becomes stably integrated into the synthetic chromosome; and monitoring production of the synthetic chromosome in the synthetic chromosome production reporter cell line.

In some aspects of the aforementioned embodiments, an arm of an endogenous chromosome present in the reporter cell line comprises a recombination site compatible for interaction with a recombination site in the synthetic chromosome.

Also in some aspects of the aforementioned embodiments, the tags of the endogenous chromosome tag and the synthetic chromosome tag are fluorescent tags, and the monitoring step is performed by fluorescence microscopy. In some configurations of this aspect, the fluorescent tags are selected from TagBFP, TagCFP, TagGFP2, TagYFP, TagRFP, FusionRed, mKate2, TurboGFP, TurboYFP, TurboRFP, TurboFP602, TurboFP635, TurboFP650, AmCyan1, AcvGFP1, ZsGreen1, ZsYellow1, mBanana, mOrange, mOrange2, DsRed-Express2, DsRed-Express, tdTomato, DsRed-Monomer, DsRed2, AsRed2, mStrawberry, mCherry, HcRed1, mRaspberry, E2-Crimson, mPlum, Dendra 2, Timer, and PAmCherry, HALO-tags, or infrared-shifted fluorescent proteins.

In other aspects of the aforementioned embodiments, the tags of the endogenous chromosome tag and the synthetic chromosome tag are chemilumenscent tags and the monitoring step is performed by chemilumenscent microscopy, or phosphorescent tags and the monitoring step is performed by phosphorescent microscopy.

In some aspects of the aforementioned embodiments, the endogenous chromosome tag comprises a marker specific to histones H1, H2A, H2B, H3, H4, or H5, and the synthetic chromosome tag comprises $4^n$ nucleotides that have been screened against a database of known sequences.

In some aspects of the aforementioned embodiments, the synthetic chromosome production reporter cell line is selected from a mammalian cell line, an embryonic cell line, a pluripotent cell line, an adult-derived stem cell, a reprogrammed cell line or a human cell line, and in preferred aspects, the synthetic chromosome production reporter cell line is human cell line HT1080.

In some aspects of the embodiments of the invention, the synthetic chromosome production reporter cell line is transfected with synthetic chromosome production components to produce synthetic chromosomes via a top down approach, in other aspects, the synthetic chromosome production reporter cell line is transfected with synthetic chromosome production components to produce synthetic chromosomes via a bottom up approach, in yet other aspects, the synthetic chromosome production reporter cell line is transfected with synthetic chromosome production components to produce synthetic chromosomes via engineering of naturally occurring minichromosomes, and in preferred aspects, the synthetic chromosome production reporter cell line is transfected with synthetic chromosome production components to produce synthetic chromosomes via de novo chromosome generation by targeted amplification of chromosomal segments, and in a preferred method for this aspect, the chromosomal segments are pericentric regions of a chromosome.

In some aspects of the aforementioned embodiments, the endogenous chromosome tag comprises a plurality of endogenous chromosome tags.

In some aspects of the aforementioned embodiments, the endogenous chromosome tag is a fusion protein, nucleic acid/protein chimera, nucleic acid/protein complex (such as RNA/CRISPR-CAS9) or a moiety comprising a TALEN protein specific to the endogenous chromosomes and a fluorescent or phosphorescent label, and the synthetic chromosome tag is a nucleic acid/protein chimera.

The present invention also provides a synthetic chromosome production reporter cell line comprising an endogenous chromosome tag and a synthetic chromosome tag, wherein the endogenous chromosome tag and synthetic chromosome tag are stably incorporated into the genome of the synthetic chromosome production reporter cell line.

Additionally, the present invention also provides a synthetic chromosome produced by the synthetic chromosome production cell line, and a synthetic chromosome the production of which has been monitored in real time by the methods of the present invention.

These and other aspects and uses of the invention will be described in the detailed description.

DETAILED DESCRIPTION OF THE INVENTION

Figure 1:
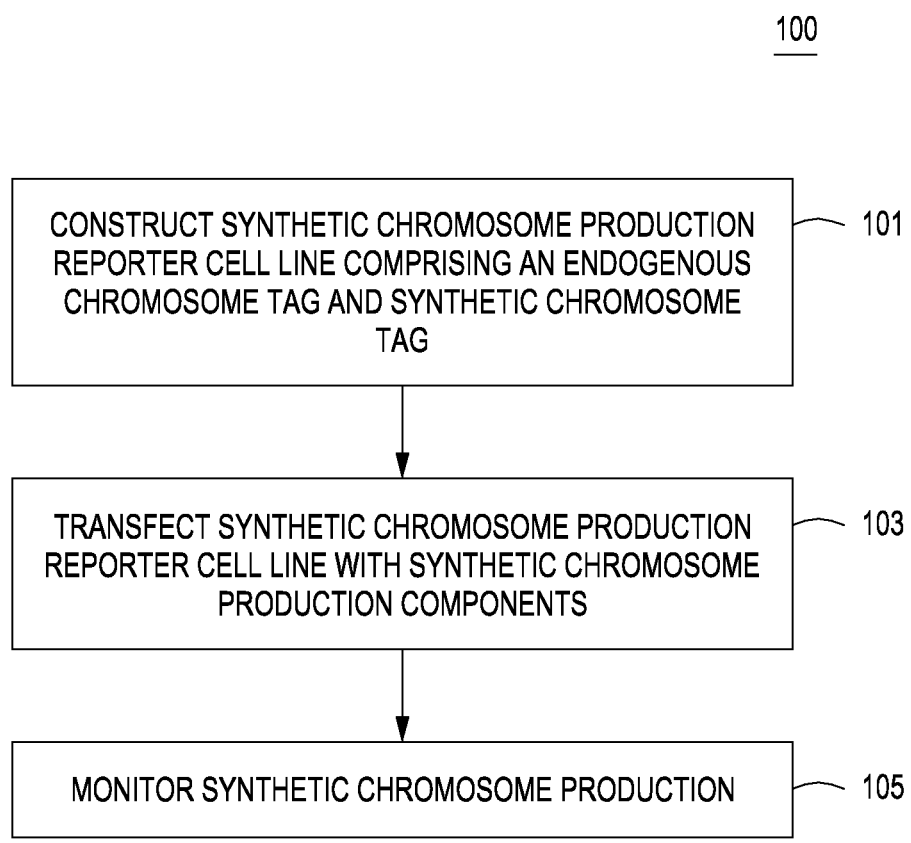
FIG. 1 is a simplified flow chart of method steps for creating a system for tracking the production of new synthetic chromosomes in real-time. In this embodiment, components of the tracking system are integrated into the production cell line's endogenous genome.

The methods described herein may employ, unless otherwise indicated, conventional techniques and descriptions of molecular biology (including recombinant techniques), cell biology, biochemistry, and cellular engineering technology, all of which are within the skill of those who practice in the art. Such conventional techniques include oligonucleotide synthesis, hybridization and ligation of oligonucleotides, transformation and transduction of cells, engineering of recombination systems, creation of transgenic animals and plants, and human gene therapy. Specific illustrations of suitable techniques can be had by reference to the examples herein. However, equivalent conventional procedures can, of course, also be used. Such conventional techniques and descriptions can be found in standard laboratory manuals such as *Genome Analysis: A Laboratory Manual Series* (Vols. I-IV) (Green, et al., eds., 1999); *Genetic Variation: A Laboratory Manual* (Weiner, et al., eds., 2007); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); *Protein Methods* (Bollag et al., John Wiley & Sons 1996); *Nonviral Vectors for Gene Therapy* (Wagner et al. eds., Academic Press 1999); *Viral Vectors* (Kaplift & Loewy, eds., Academic Press 1995); *Immunology Methods Manual* (Lefkovits ed., Academic Press 1997); *Gene Therapy Techniques, Applications and Regulations From Laboratory to Clinic* (Meager, ed., John Wiley & Sons 1999); M. Giacca, *Gene Therapy* (Springer 2010);*Gene Therapy Protocols* (LeDoux, ed., Springer 2008); *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011); *Essential Stem Cell Methods*, (Lanza and Klimanskaya, eds., Academic Press 2011); *Stem Cell Therapies: Opportunities for Ensuring the Quality and Safety of Clinical Offerings: Summary of a Joint Workshop* (Board on Health Sciences Policy, National Academies Press 2014); *Essentials of Stem Cell Biology*, Third Ed., (Lanza and Atala, eds., Academic Press 2013); and *Handbook of Stem Cells*, (Atala and Lanza, eds., Academic Press 2012), all of which are herein incorporated by reference in their entirety for all purposes. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by the appended claims.

Note that as used in the present specification and in the appended claims, the singular forms "a," "and," and "the" include plural referents unless the context clearly dictates otherwise. Thus, for example, reference to "a composition" refers to one or mixtures of compositions, and reference to "an assay" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value between the upper and lower limit of that range and any other stated or intervening value in that stated range is encompassed within the invention. The upper and lower limits of these smaller ranges may independently be included in the smaller ranges, subject to any specifically excluded limit in the stated range. Where the stated range includes both of the limits, ranges excluding only one of those included limits are also included in the invention.

In the following description, numerous specific details are set forth to provide a more thorough understanding of the present invention. However, it will be apparent to one of ordinary skill in the art upon reading the specification that the present invention may be practiced without one or more of these specific details. In other instances, well-known features and procedures well known to those skilled in the art have not been described in order to avoid obscuring the invention.

Definitions

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

"Binding" as used herein (e.g., with reference to an nucleic acid-binding domain of a polypeptide) refers to a non-covalent interaction between a polypeptide and a nucleic acid. While in a state of non-covalent interaction, the polypeptide and nucleic acid are said to be "associated", "interacting", or "binding". Binding interactions are generally characterized by a dissociation constant (Kd) of less than $10^{-6}$ M to less than $10^{-15}$ M. "Affinity" refers to the strength of binding, increased binding affinity being correlated with a lower Kd.

By "binding domain" it is meant a polypeptide or protein domain that is able to bind non-covalently to another molecule. A binding domain can bind to, for example, a DNA molecule (a DNA-binding protein), an RNA molecule (an RNA-binding protein) and/or a protein molecule (a protein-binding protein).

A "centromere" is any nucleic acid sequence that confers an ability of a chromosome to segregate to daughter cells through cell division. A centromere may confer stable segregation of a nucleic acid sequence, including a synthetic chromosome containing the centromere, through mitotic and meiotic divisions. A centromere does not necessarily need to be derived from the same species as the cells into which it is introduced, but preferably the centromere has the ability to promote DNA segregation in cells of that species. A "dicentric" chromosome is a chromosome that contains two centromeres. A "formerly dicentric chromosome" is a chromosome that is produced when a dicentric chromosome fragments. A "chromosome" is a nucleic acid molecule—and associated proteins—that is capable of replication and segregation in a cell upon division of the cell. Typically, a chromosome contains a centromeric region, replication origins, telomeric regions and a region of nucleic acid between the centromeric and telomeric regions. An "acrocentric chromosome" refers to a chromosome with arms of unequal length.

A "coding sequence" or a sequence that "encodes" a peptide is a nucleic acid molecule that is transcribed (in the case of DNA) and translated (in the case of mRNA) into a polypeptide in vivo when placed under the control of appropriate control sequences. The boundaries of the coding sequence typically are determined by a start codon at the 5' (amino) terminus and a translation stop codon at the 3' (carboxy) terminus.

The term DNA "control sequences" refers collectively to promoter sequences, polyadenylation signals, transcription termination sequences, upstream regulatory domains, origins of replication, internal ribosome entry sites, enhancers, and the like, which collectively provide for the replication, transcription and translation of a coding sequence in a recipient cell. Not all of these types of control sequences need to be present so long as a selected coding sequence is capable of being replicated, transcribed and translated in an appropriate host cell.

"Endogenous chromosomes" refer to chromosomes found in a cell prior to generation or introduction of a synthetic chromosome.

As used herein, "euchromatin" refers to chromatin that stains diffusely and that typically contains genes, and "heterochromatin" refers to chromatin that remains unusually condensed and is thought to be transcriptionally inactive. Highly repetitive DNA sequences (satellite DNA) are usually located in regions of the heterochromatin surrounding the centromere.

The terms "heterologous DNA" or "foreign DNA" (or "heterologous RNA" or "foreign RNA") are used interchangeably and refer to DNA or RNA that does not occur naturally as part of the genome in which it is present, or is found in a location or locations and/or in amounts in a genome or cell that differ from that in which it occurs in nature. Examples of heterologous DNA include, but are not limited to, DNA that encodes a gene product or gene product(s) of interest. Other examples of heterologous DNA include, but are not limited to, DNA that encodes traceable marker proteins as well as regulatory DNA sequences.

"Operably linked" refers to an arrangement of elements where the components so described are configured so as to perform their usual function. Thus, control sequences operably linked to a coding sequence are capable of effecting the expression of the coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome), and may still have interactions resulting in altered regulation.

A "promoter" or "promoter sequence" is a DNA regulatory region capable of binding RNA polymerase in a cell and initiating transcription of a polynucleotide or polypeptide coding sequence such as messenger RNA, ribosomal RNAs, small nuclear of nucleolar RNAs or any kind of RNA transcribed by any class of any RNA polymerase I, II or III.

"Recognition sequences" are particular sequences of nucleotides that a protein, DNA, or RNA molecule, or combinations thereof (such as, but not limited to, a restriction endonuclease, a modification methylase or a recombinase) recognizes and binds. For example, a recognition sequence for Cre recombinase is a 34 base pair sequence containing two 13 base pair inverted repeats (serving as the recombinase binding sites) flanking an 8 base pair core and designated loxP (see, e.g., Sauer, Current Opinion in Biotechnology, 5:521-527 (1994)). Other examples of recognition sequences, include, but are not limited to, attB and attP, attR and attL and others that are recognized by the recombinase enzyme bacteriophage Lambda Integrase. The recombination site designated attB is an approximately 33 base pair sequence containing two 9 base pair core-type Int binding sites and a 7 base pair overlap region; attP is an approximately 240 base pair sequence containing core-type Int binding sites and arm-type Int binding sites as well as sites for auxiliary proteins IHF, FIS, and Xis (see, e.g., Landy, Current Opinion in Biotechnology, 3:699-7071 (1993)).

A "recombinase" is an enzyme that catalyzes the exchange of DNA segments at specific recombination sites. An integrase refers to a recombinase that is usually derived from viruses or transposons, as well as perhaps ancient viruses. "Recombination proteins" include excisive proteins, integrative proteins, enzymes, co-factors and associated proteins that are involved in recombination reactions using one or more recombination sites (see, Landy, Current Opinion in Biotechnology, 3:699-707 (1993)). The recombination proteins used in the methods herein can be delivered to a cell via an expression cassette on an appropriate vector, such as a plasmid, and the like. In other embodiments, recombination proteins can be delivered to a cell in protein form in the same reaction mixture used to deliver the desired nucleic acid(s). In yet other embodiments, the recombinase could also be encoded in the cell and expressed upon demand using a tightly controlled inducible promoter.

"Ribosomal RNA" (rRNA) is the specialized RNA that forms part of the structure of a ribosome and participates in the synthesis of proteins. Ribosomal RNA is produced by transcription of genes which, in eukaryotic cells, are present in multiple copies. In human cells, the approximately 250 copies of rRNA genes (i.e., genes which encode rRNA) per haploid genome are spread out in clusters on at least five different chromosomes (chromosomes 13, 14, 15, 21 and 22). In human cells, multiple copies of the highly conserved rRNA genes are located in a tandemly arranged series of rDNA units, which are generally about 40-45 kb in length and contain a transcribed region and a nontranscribed region known as spacer (i.e., intergenic spacer) DNA which can vary in length and sequence.

As used herein the term "selectable marker" refers to a gene introduced into a cell, particularly in the context of this invention into cells in culture, that confers a trait suitable for artificial selection. General use selectable markers are well-known to those of ordinary skill in the art. In preferred embodiments, selectable markers for use in a human synthetic chromosome system should be non-immunogenic in the human and include, but are not limited to: human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in $CD34^+$cells); CD24 cell surface antigen in hematopoietic stem cells; human CAD gene to confer resistance to N-phosphonoacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); and Cytidine deaminase (CD; selectable by Ara-C). Drug selectable markers such as puromycin, hygromycin, blasticidin, G418, tetracycline may also be employed. In addition, using FACs sorting, any fluorescent marker gene may be used for positive selection, as may chemiluminescent markers (e.g. Halotags), and the like. Cell surface proteins linked to a moiety that can bind magnetic beads or surfaces for isolation or enrichment of the cells of interest is an additional selective marker mechanism.

"Site-specific recombination" refers to site-specific recombination that is effected between two specific sites on a single nucleic acid molecule or between two different molecules that requires the presence of an exogenous protein, such as an integrase or recombinase. Certain site-specific recombination systems can be used to specifically delete, invert, or insert DNA, with the precise event controlled by the orientation of the specific sites, the specific system and the presence of accessory proteins or factors. In addition, segments of DNA can be exchanged between chromosomes as described in FIG. 4 (chromosome arm exchange).

"Synthetic chromosomes" (also referred to as "artificial chromosomes") are nucleic acid molecules, typically DNA, that stably replicate and segregate alongside endogenous chromosomes in cells that have the capacity to accommodate and express heterologous genes. A "mammalian synthetic chromosome" refers to chromosomes that have an active mammalian centromere(s). A "human synthetic chromosome" refers to a chromosome that includes a centromere that functions in human cells and that preferably is produced in human cells. For exemplary artificial chromosomes, see, e.g., U.S. Pat. Nos. 8,389,802; 7,521,240; 6,025,155; 6,077,697; 5,891,691; 5,869,294; 5,721,118; 5,712,134; 5,695,967; and 5,288,625 and published International PCT application Nos. WO 97/40183 and WO 98/08964.

The terms "subject", "individual" or "patient" may be used interchangeably herein and refer to a mammal, and in some embodiments, a human.

A "vector" is a replicon, such as plasmid, phage, viral construct, cosmid, bacterial artificial chromosome, P-1 derived artificial chromosome or yeast artificial chromosome to which another DNA segment may be attached. In some instances a vector may be a chromosome such as in the case of an arm exchange from one endogenous chromosome engineered to comprise a recombination site to a synthetic chromosome. Vectors are used to transduce and express a DNA segment in cell.

THE INVENTION

The present invention encompasses compositions and methods to allow one to monitor formation of synthetic chromosomes in real-time via standardized microscopy such as fluorescent microscopy or by other visual methods, eliminating the need for cumbersome, expensive, and possibly mutagenic analysis. Prior to the present invention, production of synthetic chromosomes was, in effect, blind, where the production of new synthetic chromosomes could not be tracked in real time, and success could only be measured after drug resistant cell colonies were cloned, expanded and assayed via low-throughput methods such as fluorescent in situ hybridization (FISH) screening of a large number of clones.

The advantages of the compositions and methods of the present invention include 1) synthetic chromosome production can be monitored in real time via standardized fluorescence microscopy (or other visual means), allowing for rapid elimination of abortive clones (i.e., drug resistant colonies that have not produced a synthetic chromosome); 2) the need for periodic FISH analysis to test for chromosome formation is decreased or eliminated; 3) the system can be used to test components for synthetic chromosome generation and stoichiometry of test components can be assessed, leading to optimization of synthetic chromosome production; 4) the system provides an assayable format permitting the screening of potential small molecule compounds that control or enhance synthetic chromosome production; 5) the need for potentially mutagenic dyes for identifying synthetic chromosomes during flow cytometric-based sorting, isolation and transfer is decreased or eliminated; and 6) the decrease or elimination of screening steps reduces the cost of reagents required and the time it takes to characterize the synthetic chromosomes. For example, Lindenbaum and Perkins, et al., Nucleic Acid Research, 32(21):e172 (2004) describe the production of a mammalian satellite DNA-based Artificial Chromosome Expression (ACE) System. In this system, new synthetic chromosomes could not be tracked in real time, and success could only be measured after drug resistant cell colonies were cloned, expanded and assayed via fluorescent in situ hybridization (FISH) screening of a large number of clones, which took approximately 3 months. The present invention allows for one to decrease or entirely eliminate repeated FISH analysis, which takes at least four days to perform.

The compositions and methods of the present invention for real-time monitoring of synthetic chromosome production is applicable to all methodologies of synthetic chromosome production, including the "top down" approach, the "bottom up" approach, engineering of naturally-occurring minichromosomes, and induced de novo chromosome generation by targeted amplification of specific chromosomal segments (all of which are discussed in more detail, infra).

FIG. 1 is a simplified flow chart of method steps for one embodiment for creating a system for tracking the production of new synthetic chromosomes in real-time. The first step 101 in method 100 is to construct a synthetic chromosome production reporter cell line in which to produce the synthetic chromosomes. Construction of the synthetic chromosome production reporter cell line essentially entails stably transforming a cell line to express at least two defined tags: one labeled tag specific to endogenous chromosomes in the chromosome engineering reporter cell line, and one differently-labeled tag specific to a sequence on the synthetic chromosome that is to be produced (that is, a "cis endogenous chromosome" system, where the tags are encoded by endogenous chromosomes in the reporter cell line). The methods and tags used to construct the synthetic chromosome production reporter cell line will differ depending on the species from which the cell is derived and the tag complement on the synthetic chromosome to be produced.

Second step 103 is to transfect or transform the synthetic chromosome production reporter cell line constructed in step 101 with components appropriate for synthetic chromosome production. The appropriate components will vary depending on the method of chromosome production employed (that is, whether the method is "top down", "bottom up", engineering of minichromosomes, or de novo chromosome generation), and the system selected for engineering the genetic payload into the synthetic chromosomes.

Finally, the third step 105 is to monitor in real time the production of the synthetic chromosome via, e.g., fluorescence microscopy or other visual means to analyze and track the endogenous chromosome-specific tags and the synthetic chromosome-specific tags. The endogenous chromosome-specific tag allows one to assess the endogenous chromosome population to ensure "health" of the synthetic chromosome production reporter cell line, and the synthetic chromosome-specific tag allows one to assess the formation and continued presence of the synthetic chromosome. Additionally, if the synthetic chromosome-specific tag is specific to site-specific integration sequences (acceptor sites) on the synthetic chromosome, the signal from the labeled tag indirectly is a measure of the number of acceptor sites.

Figure 2:
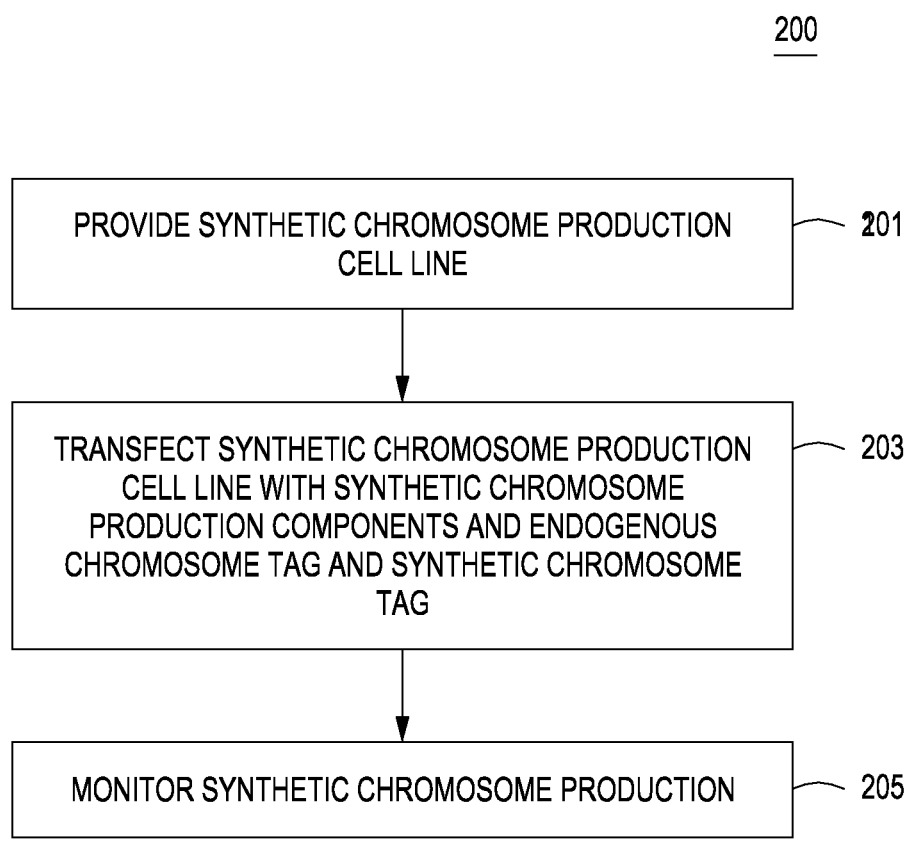
FIG. 2 is a simplified flow chart of method steps for creating an alternative system for tracking the production of new synthetic chromosomes in real-time. In this embodiment, the components of the tracking system are integrated into the synthetic chromosome and thus are co-ported into the production cell line with the synthetic chromosome.

FIG. 2 illustrates an alternative embodiment of the compositions and methods of the present invention. Like FIG. 1, FIG. 2 is a simplified flow chart of method steps for one embodiment for creating a system for tracking the production of new synthetic chromosomes in real-time. The first step 201 in method 200 is to select a synthetic chromosome production cell line in which to produce the synthetic chromosomes. Note that where in the previous embodiment, a reporter cell line was constructed to express two defined reporter tags ("cis endogenous chromosome"), in this alternative embodiment the synthetic chromosome production cell line does not express the reporter tags; instead, the synthetic chromosome is engineered to express the reporter tags (that is, a "cis synthetic chromosome", where the tags are encoded by the synthetic chromosome).

Second step 203 is to transfect the synthetic chromosome production cell line constructed in step 201 with components appropriate for synthetic chromosome production. As discussed in relation to the first embodiment, the appropriate components will vary depending on the method of chromosome production employed (that is, whether the method is "top down", "bottom up", engineering of minichromosomes, or de novo chromosome generation), and the system selected for engineering the genetic payload into the synthetic chromosomes. However, in contrast to the first embodiment, in this alternative embodiment the synthetic chromosome is engineered to express the two reporter tags: one labeled tag specific to endogenous chromosomes in the synthetic chromosome production cell line, and one differently-labeled tag specific to a sequence on the synthetic chromosome that is to be produced.

Finally, the third step 205 of method 200 is the same as the third step 105 of method 100: monitor in real time the production of the synthetic chromosome via fluorescent microscopy or other visual means by tracking the endogenous chromosome-specific tags and the synthetic chromosome-specific tags. The endogenous chromosome-specific tag allows one to assess the endogenous chromosome population to ensure "health" of the synthetic chromosome production cell line, and the synthetic chromosome-specific tag allows one to assess the formation and continued presence of the synthetic chromosome.

The alternative methods differ in that the method illustrated in FIG. 1 requires construction of a synthetic chromosome production reporter cell line, and the method in FIG. 2 requires only selecting a cell line for synthetic chromosome production without engineering the reporting feature into the cell line. In either method, the selection of the cell to be engineered, report and produce the synthetic chromosome (method of FIG. 1) or the cell to be used only to produce the synthetic chromosome (method of FIG. 2) depends at least in part on the species for which the synthetic chromosome is being produced and the type of cell in which the synthetic chromosome will ultimately be delivered. For example, to produce synthetic chromosomes to be used in humans, it is desirable to choose a human cell line for synthetic chromosome production, as fully humanized synthetic chromosomes likely circumvent problems that synthetic chromosomes produced in mammalian cells other than humans might have when delivered into a human patient, such as potential immune responses and problems with genetic stability.

Figure 3:
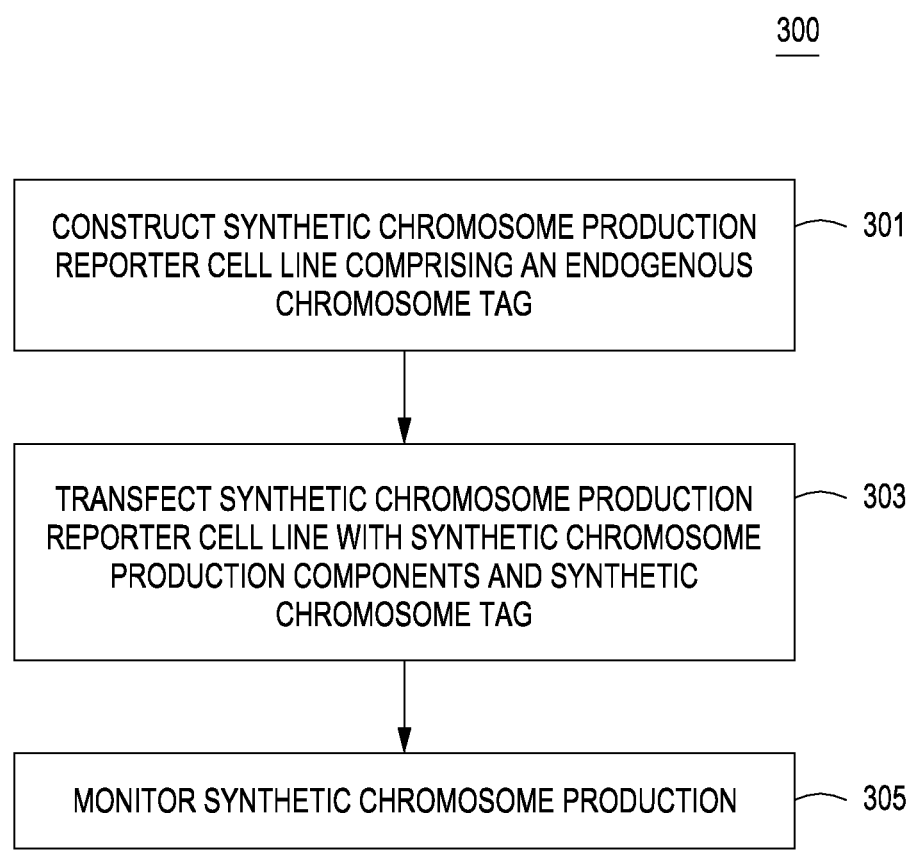
FIG. 3 is a simplified flow chart of method steps for creating yet another alternative system for tracking the production of new synthetic chromosomes in real-time. In this embodiment, one component of the tracking system is integrated into the synthetic chromosome and one component of the tracking system is integrated into the production cell line's endogenous genome.

FIG. 3 illustrates yet another alternative embodiment of the compositions and methods of the present invention. Like FIGS. 1 and 2, FIG. 3 is a simplified flow chart of method steps for one embodiment for creating a system for tracking the production of new synthetic chromosomes in real-time. The first step 301 in method 300 is to construct a synthetic chromosome production reporter cell line in which to produce the synthetic chromosomes. Construction of the synthetic chromosome production reporter cell line essentially entails stably transforming a cell line to express one of the two tags: the labeled tag specific to endogenous chromosomes. In step 303, the synthetic chromosome reporter cell line is transfected with a synthetic chromosome production components and a synthetic chromosome tag, which is incorporated into the synthetic chromosome. In this embodiment, the reporter cell line is engineered to express the labeled tag specific to the endogenous chromosomes, and the synthetic chromosome is engineered to express the differentially labeled tag specific for the synthetic chromosome (that is, a "trans chromosome" system, where the tags are expressed by different chromosomes: an endogenous chromosome and the synthetic chromosome). Note that in the previous embodiments, either the reporter cell line was constructed to express two defined reporter tags ("cis endogenous chromosome" system), or the synthetic chromosome was engineered to express the two defined reporter tags ("cis synthetic chromosome" system).

Finally, the third step 305 of method 300 is the same as the third step 105 of method 100 and 205 of method 200: monitor in real time the production of the synthetic chromosome via fluorescent microscopy or other visual means by tracking the endogenous chromosome-specific tags and the synthetic chromosome-specific tags. The endogenous chromosome-specific tag allows one to assess the endogenous chromosome population to ensure "health" of the synthetic chromosome production cell line, and the synthetic chromosome-specific tag allows one to assess the formation and continued presence of the synthetic chromosome.

Note that one could construct another alternative system—an "opposite trans chromosome" system, where the synthetic chromosome production reporter cell line is stably transformed to express the differentially labeled tag specific to synthetic chromosome and the synthetic chromosome is engineered to express the labeled tag specific for the endogenous chromosomes. Essentially, whether one selects the system of FIG. 1 ("cis endogenous chromosome" system), FIG. 2 ("cis synthetic chromosome system"), FIG. 3 ("trans chromosome" system) or the "opposite trans chromosome system" is simply a design choice based on the design of the vectors, method for creating the synthetic chromosome, cell line being engineered, etc.

Once a synthetic chromosome is produced, it can be used in any number of pharmacological, therapeutic and biological applications, for example, production of recombinant proteins in transgenic animals, analysis of regulation and expression of large human genes in a variety of cell types or animal models, and chromosome-based gene-delivery vectors for ex vivo gene therapy, directing cell differentiation and dedifferentiation, formation of induced pluripotent stem cells, creation of novel autocrine and paracrine cellular communication networks, creation of multi-expression systems capable of stoichiometric production of multiple encoded factors, production of biological circuits, insertion of DNA elements capable of probing the nuclear architecture and downstream uses for regulating genomic expression using discovered interactions in the nuclear architecture, and manipulation of large DNA elements (>50 Kb, >100 Kb, >200 Kb or larger) such as but not limited to chromosome arm exchange onto the synthetic chromosome or incorporation of multiple large DNA elements onto the synthetic chromosome.

Figure 4:
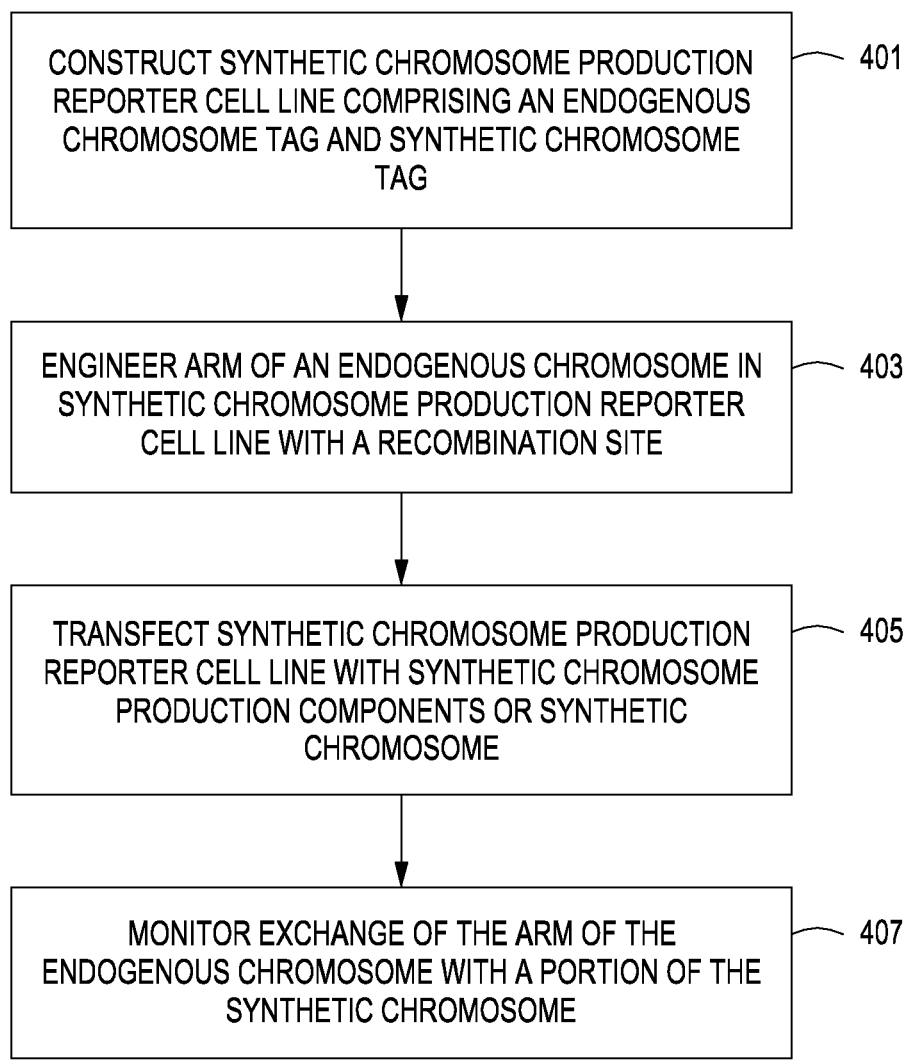
FIG. 4 is a simplified flow chart of method steps for monitoring the exchange of a "chromosome arm" from an endogenous genome to the synthetic chromosome.

FIG. 4 is a simplified flow chart of method steps showing how the methods of the present invention could be used for monitoring the exchange of a "chromosome arm" from an endogenous genome to the synthetic chromosome. In step 401 of method 400, a synthetic chromosome production reporter cell line comprising an endogenous chromosome tag and synthetic chromosome tag is constructed. In step 403, an arm of an endogenous chromosome in the synthetic chromosome production reporter cell line is selected to be engineered with a recombination site. In step 405, the synthetic chromosome production reporter cell line k transfected with synthetic chromosome production components, and in step 407, the exchange of the arm of the endogenous chromosome with a portion of the synthetic chromosome is monitored by ascertaining whether the label that paints the endogenous chromosome is detected as being associated with the synthetic chromosome.

Synthetic Chromosome Producing Cells

In some embodiments, the cells to be engineered and/or produce the synthetic chromosome can be cells that naturally occur in a subject (human patient, animal or plant) in which the genes or regulatory sequences from the synthetic chromosome will ultimately be expressed. Such cells can be primary-culture cell lines established for the purpose of synthetic chromosome production specific for an individual. In other embodiments, the cells to be engineered and/or produce the synthetic chromosome are from an established cell line. A wide variety of cell lines for tissue culture are known in the art. Examples of cell lines include but are not limited to human cells lines such as 293-T (embryonic kidney), 721 (melanoma), A2780 (ovary), A172 (glioblastoma), A253 (carcinoma), A431 (epithelium), A549 (carcinoma), BCP-1 (lymphoma), BEAS-2B (lung), BR 293 (breast), BxPC3 (pancreatic cancinoma), Cal-27 (tongue), COR-L23 (lung), COV-434 (ovary), CML T1 (leukemia), DUI45 (prostate), DuCaP (prostate), FM3 (lymph node), H1299 (lung), H69 (lung), HCA2 (fibroblast), HEK0293 (embryonic kidney), HeLa (cervix), HL-60 (myeloblast), HMEC (epithelium), HT-29 (colon), HUVEC (umbilical vein epithelium), Jurkat (T cell leukemia), JY (lymphoblastoid), K562 (lymphoblastoid), KBM-7 (lymphoblastoid), Ku812 (lymphoblastoid), KCL22 (lymphoblastoid), KGI (lymphoblastoid), KYO1 (lymphoblastoid), LNCap (prostate), Ma-Mel (melanoma), MCF-7 (mammary gland), MDF-10A (mammary gland), MDA-MB-231, −468 and −435 (breast), MG63 (osteosarcoma), MOR/0.2R (lung), MONO-MAC6 (white blood cells), MRC5 (lung), MSU1.1 (fibroblast), NCI—H69 (lung), NALM-1 (peripheral blood), NW-145 (melanoma), OPCN/OPCT (prostate), Peer (leukemia), Raji (B lymphoma), Saos-2 (osteosarcoma), Sf21 (ovary), Sf9 (ovary), SiHa (cervical cancer), SKBR3 (breast carcinoma), SKOV-2 (ovary carcinoma), T-47D (mammary gland), T84 (lung), U373 (glioblastoma), U87 (glioblastoma), U937 (lymphoma), VCaP (prostate), WM39 (skin), WT-49 (lymphoblastoid), and YAR (B cell). Rodent cell lines of interest include but are not limited to 3 T3 (mouse fibroblast), 4T1 (mouse mammary), 9 L (rat glioblastoma), A20 (mouse lymphoma), ALC (mouse bone marrow), B16 (mouse melanoma), B35 (rat neuroblastoma), bEnd.3 (mouse brain), C2C12 (mouse myoblast), C6 (rat glioma), CGR8 (mouse embryonic), CT26 (mouse carcinoma), E14Tg2a (mouse embryo), EL4 mouse leukemia), EMT6/AR1 (mouse mammary), Hepalclc7 (mouse hepatoma), J558L (mouse myeloma), MC-38 (mouse adenocarcinoma), MTD-1A (mouse epithelium), RBL (rat leukemia), RenCa (mouse carcinoma), X63 (mouse lymphoma), YAC-1 (mouse Be cell), BHK-1 (hamster kidney), and CHO (hamster ovary). Plant cell lines of use include but are not limited to BY-2, Xan-1, GV7, GF11, GT16, TBY-AtRER1B, 3n-3, and G89 (tobacco); VR, VW, and YU-1 (grape); PAR, PAP, and PAW (pokeweed); Spi-WT, Spi-1-1, and Spi12F (spinach); PSB, PSW and PSG (sesame); A.per, A.pas, A.plo (asparagus); Pn and Pb (bamboo); and DG330 (soybean); embryonic cell lines; pluripotent cell lines; adult derived stem cells; reprogrammed cell lines; generic animal cell lines of any species or broadly embryonic or reprogrammed cells; zebra fish cell lines; primary dog cells; primary horse cells; chicken DT40 cells; dog cell lines; cat cell lines; patient cell lines; and, in some preferred embodiments, the HT1080 human cell line is utilized. Potential cells of use include any living cell, but those from eucaryotes are specifically contemplated. These cell lines and others are available from a variety of sources known to those with skill in the art (see, e.g., the American Type Culture Collection (ATCC) (Manassas, Va.)). A cell transfected with one or more vectors described herein is used to establish a new cell line that comprises one or more vector-derived sequences.

Vectors to Deliver Labeled Tags

The choice of vector to be used in delivery of the labeled tag specific to the endogenous chromosomes and the labeled tag specific to the synthetic chromosome will depend upon a variety of factors such as the type of cell in which propagation is desired. Certain vectors are useful for amplifying and making large amounts of the desired DNA sequence, while other vectors are suitable for expression in cells in culture. Still other vectors are suitable for transfer and expression in cells in a whole animal. The choice of appropriate vector is well within the skill of those in the art, and many vectors are available commercially. To prepare the constructs, a polynucleotide is inserted into a vector, typically by means of ligation of a sequence into a cleaved restriction enzyme site in the vector. Alternatively, the desired nucleotide sequence can be inserted by homologous recombination or site-specific recombination. Typically homologous recombination is accomplished by attaching regions of homology to the vector on the flanks of the desired nucleotide sequence (e.g., cre-lox, att sites, etc.). Nucleic acids containing such sequences can be added by, for example, ligation of oligonucleotides, or by polymerase chain reaction using primers comprising both the region of homology and a portion of the desired nucleotide sequence. Exemplary vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include λgt10, λgt11, λgt18-23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS 203, pWE15, pWE16 and the charomid 9 series of vectors. Additional vectors include bacterial artificial chromosomes (BACs) based on a functional fertility plasmid (F-plasmid), yeast artificial chromosomes (YACs), and P1-derived artificial chromosomes, DNA constructs derived from the DNA of P1 bacteriophage (PACS). Alternatively and preferably, recombinant virus vectors may be engineered, including but not limited to those derived from viruses such as herpes virus, retroviruses, vaccinia virus, poxviruses, adenoviruses, lentiviruses, adeno-associated viruses or bovine papilloma virus.

In preferred embodiments, the labels utilized in the present invention that are associated with the tags used to mark or "paint" the endogenous chromosomes and the synthetic chromosome are expressed fluorescent proteins; thus, an expression cassette may be employed. An expression vector provides transcriptional and translational regulatory sequences, and may provide for inducible or constitutive expression, where the coding region is operably linked under the transcriptional control of the transcriptional initiation region and a transcriptional and translational termination region. These control regions may be native to the gene encoding the polypeptide or may be derived from exogenous sources, including species-specific endogenous promoters. In general, the transcriptional and translational regulatory sequences may include, but are not limited to, promoter sequences, ribosomal binding sites, transcriptional start and stop sequences, translational start and stop sequences, and enhancer or activator sequences. In addition to constitutive and inducible promoters, strong promoters (e.g., T7, CMV, and the like) find use in the constructs described herein, particularly where high expression levels are desired in an in vivo (cell-based) or in an in vitro expression system. Other exemplary promoters include mouse mammary tumor virus (MMTV) promoters, Rous sarcoma virus (RSV) promoters, adenovirus promoters, the promoter from the immediate early gene of human CMV, and the promoter from the long terminal repeat (LTR) of RSV. Alternatively, the promoter can also be provided by, for example, a 5' UTR of a retrovirus.

Expression vectors generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems; thus allowing it to be maintained in organisms, for example in mammalian cells for expression and in a prokaryotic host for cloning and amplification. In addition the expression construct may contain a selectable marker gene to allow the selection of transformed host cells. Selection genes are well known in the art and will vary with the host cell used.

Synthetic Chromosome Production

The real-time monitoring of synthetic chromosome production methods of the present invention are applicable to all currently-employed methods of synthetic chromosome production. As discussed briefly, above, the real-time monitoring methods of the present invention are applicable to all of the "top down", "bottom up", engineering of minichromosomes, and induced de novo chromosome generation methods used in the art. The "bottom up" approach of synthetic chromosome formation relies on cell-mediated de novo chromosome formation following transfection of a permissive cell line with cloned α-satellite sequences, which comprise typical host cell-appropriate centromeres and selectable marker gene(s), with or without telomeric and genomic DNA. (For protocols and a detailed description of these methods see, e.g., Harrington, et al., Nat. Genet., 15:345-55 (1997); Ikeno, et al., Nat. Biotechnol., 16:431-39 (1998); Masumoto, et al., Chromosoma, 107:406-16 (1998), Ebersole, et al., Hum. Mol. Gene., 9:1623-31 (2000); Henning, et al., PNAS USA, 96:592-97 (1999); Grimes, et al., EMBO Rep. 2:910-14 (2001); Mejia, et al., Genomics, 79:297-304 (2002); and Grimes, et al., Mol. Ther., 5:798-805 (2002).) Both synthetic and naturally occurring α-satellite arrays, cloned into yeast artificial chromosomes, bacterial artificial chromosomes or P1-derived artificial chromosome vectors have been used in the art for de novo synthetic chromosome formation. The products of bottom up assembly can be linear or circular, comprise simplified and/or concatamerized input DNA with an α-satellite DNA based centromere, and typically range between 1 and 10 Mb in size. Bottom up-derived synthetic chromosomes also are engineered to incorporate nucleic acid sequences that permit site-specific integration of target DNA sequence onto the synthetic chromosome.

The "top down" approach of producing synthetic chromosomes involves sequential rounds of random and/or targeted truncation of pre-existing chromosome arms to result in a pared down synthetic chromosome comprising a centromere, telomeres, and DNA replication origins. (For protocols and a detailed description of these methods see, e.g., Heller, et al., PNAS USA, 93:7125-30 (1996); Saffery, et al., PNAS USA, 98:5705-10 (2001); Choo, Trends Mol. Med., 7:235-37 (2001); Barnett, et al., Nuc. Ac. Res., 21:27-36 (1993); Farr, et al., PNAS USA, 88:7006-10 (1991); and Katoh, et al., Biochem. Biophys. Res. Commun., 321:280-90 (2004).) "Top down" synthetic chromosomes are constructed optimally to be devoid of naturally-occurring expressed genes and are engineered to contain DNA sequences that permit site-specific integration of target DNA sequences onto the truncated chromosome, mediated, e.g., by site-specific DNA integrases.

A third method of producing synthetic chromosomes known in the art is engineering of naturally occurring minichromosomes. This production method typically involves irradiation-induced fragmentation of a chromosome containing a functional, e.g., human neocentromere possessing centromere function yet lacking α-satellite DNA sequences and engineered to be devoid of non-essential DNA. (For protocols and a detailed description of these methods see, e.g., Auriche, et al., EMBO Rep. 2:102-07 (2001); Moralli, et al., Cytogenet. Cell Genet., 94:113-20 (2001); and Caine, et a., Somat. Cell Mol. Genet., 15:445-460 (1989).) As with other methods for generating synthetic chromosomes, engineered minichromosomes can be engineered to contain DNA sequences that permit site-specific integration of target DNA sequences.

The fourth approach for production of synthetic chromosomes involves induced de novo chromosome generation by targeted amplification of specific chromosomal segments. This approach involves large-scale amplification of pericentromeric/ribosomal DNA regions situated on acrocentric chromosomes. The amplification is triggered by co-transfection of excess DNA specific to the pericentric region of chromosomes, such as ribosomal RNA, along with DNA sequences that allow for site-specific integration of target DNA sequences and also a drug selectable marker which integrates into the pericentric regions of the chromosomes. (For protocols and a detailed description of these methods see, e.g., Csonka, et al., J. Cell Sci 113:3207-16 (2002); Hadlaczky, et al., Curr. Opini. Mol. Ther., 3:125-32 (2001); and Lindenbaum and Perkins, et al., Nuc. Ac. Res., 32(21): e172 (2004).) During this process, targeting to the pericentric regions of acrocentric chromosomes with co-transfected DNA induces large-scale chromosomal DNA amplification, duplication/activation of centromere sequences, and subsequent breakage and resolution of dicentric chromosomes resulting in a "break-off" satellite DNA-based synthetic chromosome containing multiple site-specific integration sites. One exemplary embodiment of this process is shown in FIG. 5.

Figure 5:
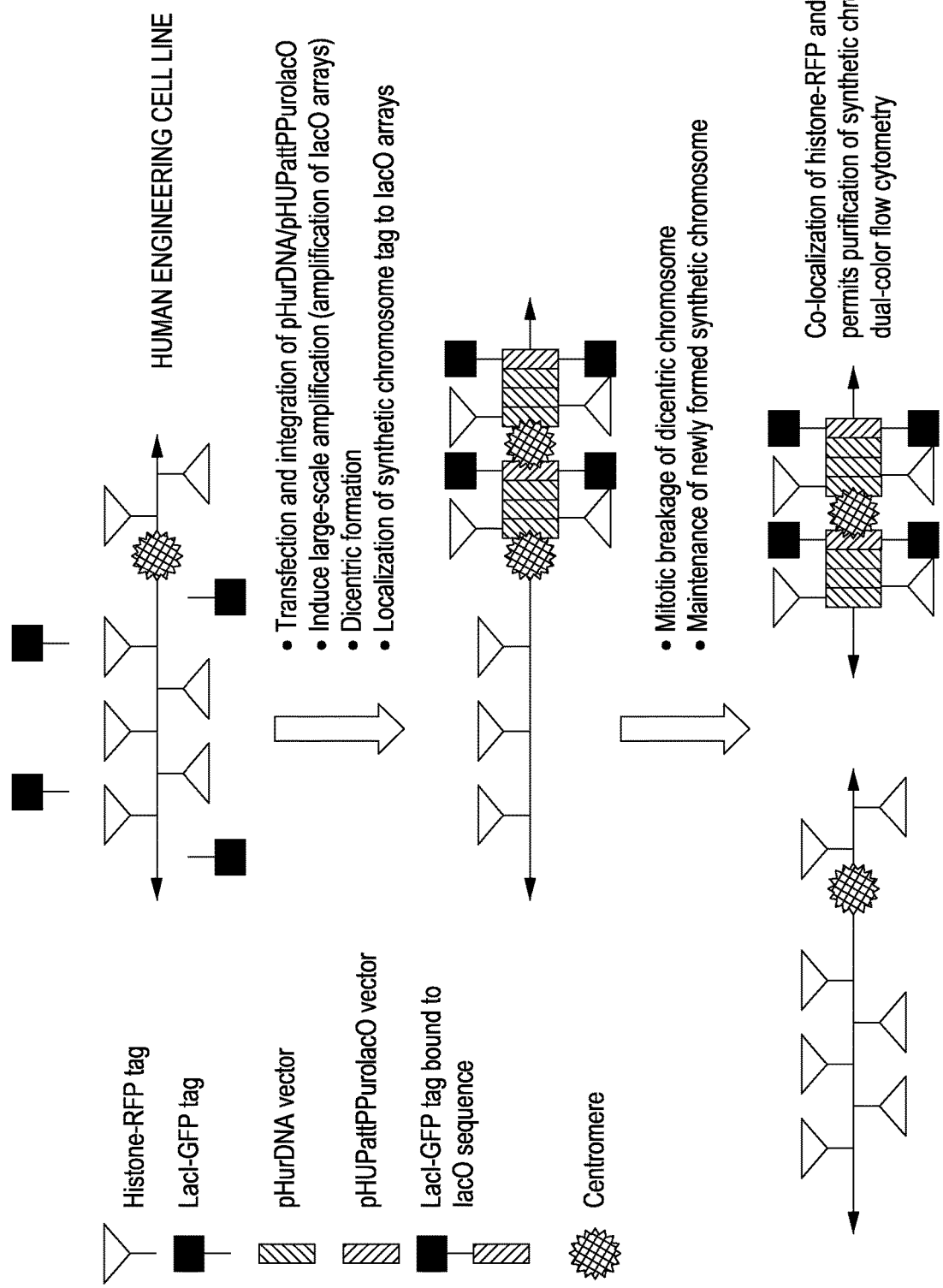
FIG. 5 shows the details of one exemplary process (in this case, via induced de novo chromosome generation by targeted amplification of specific chromosomal segments) of creating a synthetic chromosome in a synthetic chromosome production cell line, which process is monitored by the methods of the present invention.

FIG. 5 is a graphic representation of one embodiment of the method for real-time monitoring of chromosome production. Exemplary components are listed and indicated as noted: a histone H2B red fluorescent protein tag, which is specific for endogenous chromosomes in the human engineering cell line; a LacI green fluorescent protein tag, which is specific for the synthetic chromosome; a pHurDNA vector and a pHUPattPPurolacO vector which deliver the components to create the synthetic chromosome; the LacI green fluorescent protein bound to the lacO sequences on the synthetic chromosome; and the histone H2B red fluorescent protein bound to chromosomes. In the process, a human engineering cell line is transfected with the two vectors that deliver the components to create the synthetic chromosome, and these vectors are integrated into the endogenous chromosome in the human engineering cell line. Large-scale amplification of lacO arrays is induced, and a dicentric chromosome is formed from an endogenous chromosome and the components of the synthetic chromosome. In addition, the LacI green fluorescent protein tags are localized to the lacO arrays on the synthetic chromosome. After mitotic breakage of the dicentric chromosome, the newly-formed synthetic chromosome is maintained in the human engineering cell line. Co-localization of the histone red fluorescent protein tags and the LacI green fluorescent tags allows for purification of the synthetic chromosome by dual-color flow cytometry.

Figure 6:
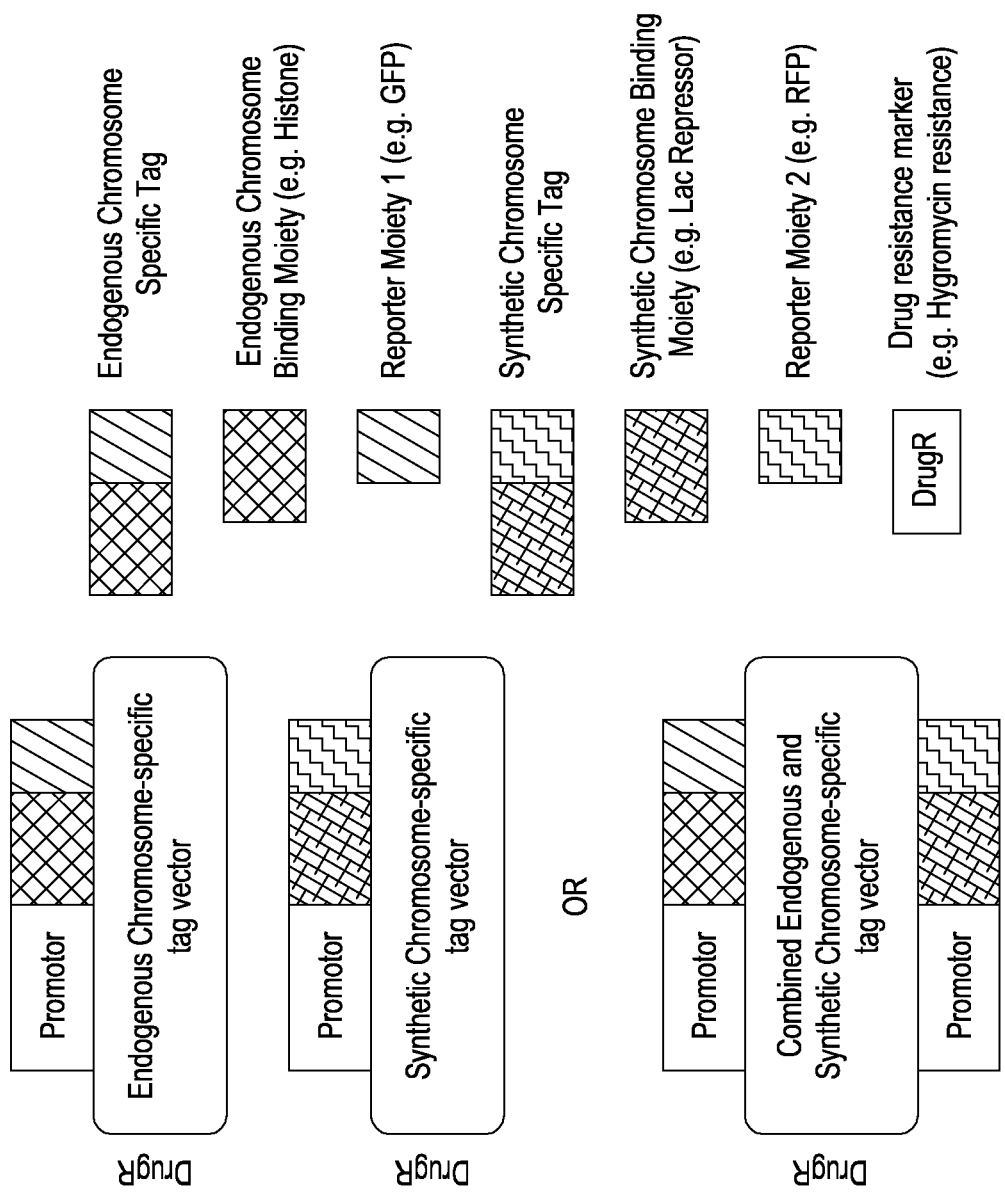
FIG. 6 shows simplified constructs of the endogenous chromosome specific tag vector, synthetic chromosome specific tag vector and a combined endogenous and synthetic chromosome specific vector.

FIG. 6 shows simplified constructs of the endogenous chromosome specific tag vector, synthetic chromosome specific tag vector and a combined endogenous and synthetic chromosome specific vector. Exemplary components are listed and indicated as noted: the endogenous chromosome specific tag; the endogenous chromosome binding moiety (e.g., a histone binding moiety); a first reporter moiety (e.g., a first fluorescent protein); the synthetic chromosome specific tag; the synthetic chromosome binding moiety (e.g., lac repressor); a second reporter moiety (e.g., a second fluorescent protein); and a selectable marker (e.g., a drug resistance gene such as for hygromycin resistance).

Component Delivery into the Synthetic Chromosome Production Cells

The vectors carrying the reporter tags of the present invention and/or the components appropriate for synthetic chromosome production can be delivered to the cells to be engineered and/or produce the synthetic chromosome by any method known in the art. The terms transfection and transformation refer to the taking up of exogenous nucleic acid, e.g., an expression vector, by a host cell whether or not any coding sequences are, in fact, expressed. Numerous methods of transfection are known to the ordinarily skilled artisan, for example, by Agrobacterium-mediated transformation, protoplast transformation (including polyethylene glycol (PEG)-mediated transformation, electroporation, protoplast fusion, and microcell fusion), lipid-mediated delivery, liposomes, electroporation, sonoporation, microinjection, particle bombardment and silicon carbide whisker-mediated transformation and combinations thereof (see, e.g., Paszkowski, et al., EMBO J., 3:2717-2722 (1984); Potrykus, et al., Mol. Gen. Genet., 199:169-177 (1985); Reich, et al., Biotechnology, 4:1001-1004 (1986); Klein, et al., Nature, 327:70-73 (1987); U.S. Pat. No. 6,143,949; Paszkowski, et al., in *Cell Culture and Somatic Cell Genetics of Plants*, Vol. 6,Molecular Biology of Plant Nuclear Genes, (Schell and Vasil, eds., Academic Publishers 1989); and Frame, et al., Plant J., 6:941-948 (1994)); direct uptake using calcium phosphate (Wigler, et al., Proc. Natl. Acad. Sci. U.S.A., 76:1373-1376 (1979)); polyethylene glycol (PEG)-mediated DNA uptake; lipofection (see, e.g., Strauss, Meth. Mol. Biol., 54:307-327 (1996)); microcell fusion (Lambert, Proc. Natl. Acad. Sci. U.S.A., 88:5907-5911 (1991); U.S. Pat. No. 5,396,767; Sawford, et al., Somatic Cell Mol. Genet., 13:279-284 (1987); Dhar, et al., Somatic Cell Mol. Genet., 10:547-559 (1984); and McNeill-Killary, et al., Meth. Enzymol., 254:133-152 (1995)); lipid-mediated carrier systems (see, e.g., Teifel, et al., Biotechniques, 19:79-80 (1995); Albrecht, et al., Ann. Hematol., 72:73-79 (1996); Holmen, et al., In Vitro Cell Dev. Biol. Anim., 31:347-351 (1995); Remy, et al., Bioconjug. Chem., 5:647-654 (1994); Le Bolch, et al., Tetrahedron Lett., 36:6681-6684 (1995); and Loeffler, et al., Meth. Enzymol., 217:599-618 (1993)); or other suitable methods. Methods for delivery of synthetic chromosomes also are described in U.S. application Ser. No. 09/815,979. Successful transfection is generally recognized by detection of the presence of the heterologous nucleic acid within the transfected cell, such as, for example, any visualization of the heterologous nucleic acid, expression of a selectable marker or any indication of the operation of a vector within the host cell. For a description of delivery methods useful in practicing the present invention, see U.S. Pat. Nos. 5,011,776; 5,747,308; 4,966,843; 5,627,059; 5,681,713; Kim and Eberwine, Anal. Bioanal. Chem. 397 (8): 3173-3178 (2010).

Labeled Tags

Figure 8:
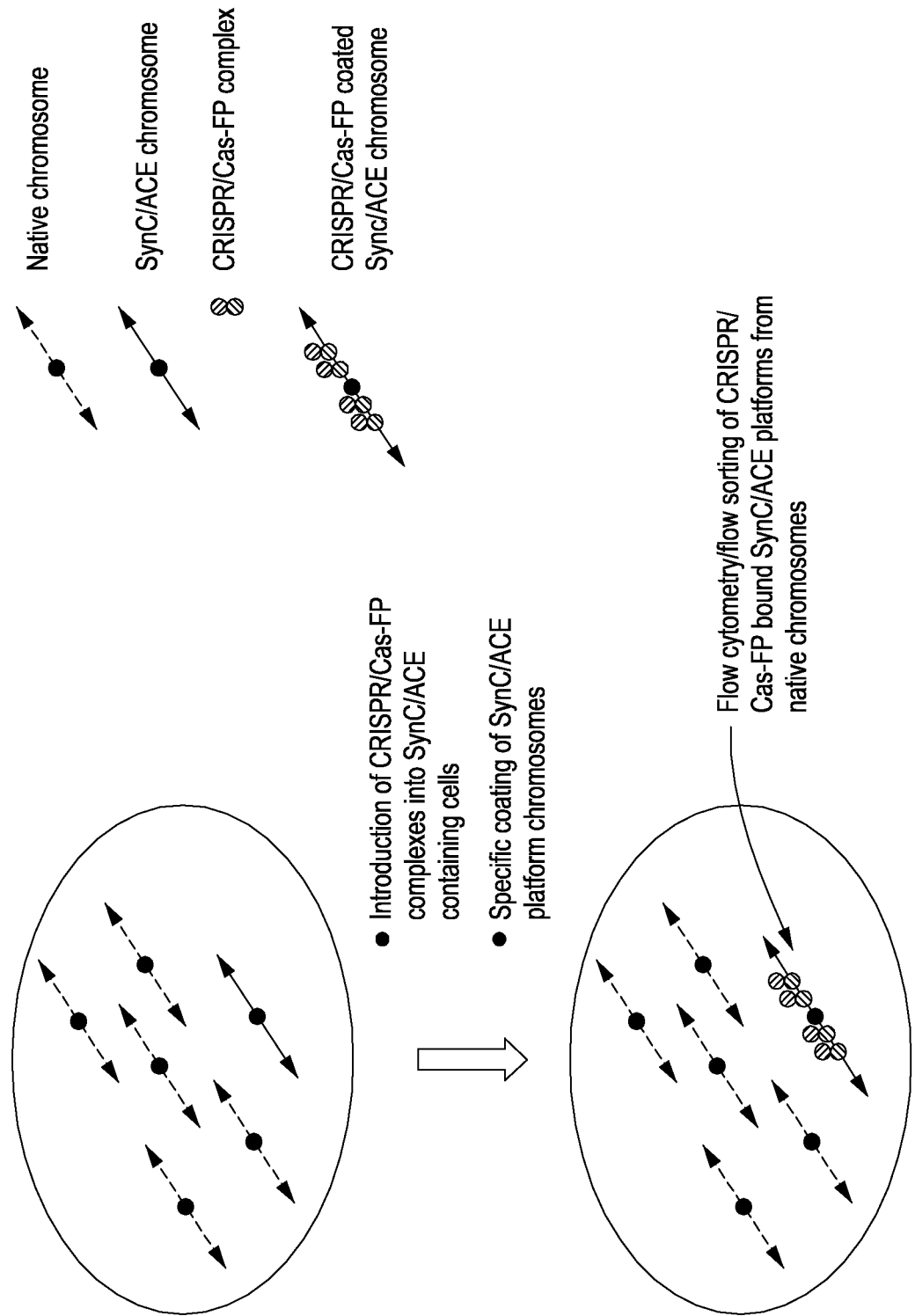
FIG. 8 is a graphic representation of using a CRISPR/Cas fluorescent visualization system for monitoring, isolating, and/or purifying a synthetic chromosome.
Figure 9:
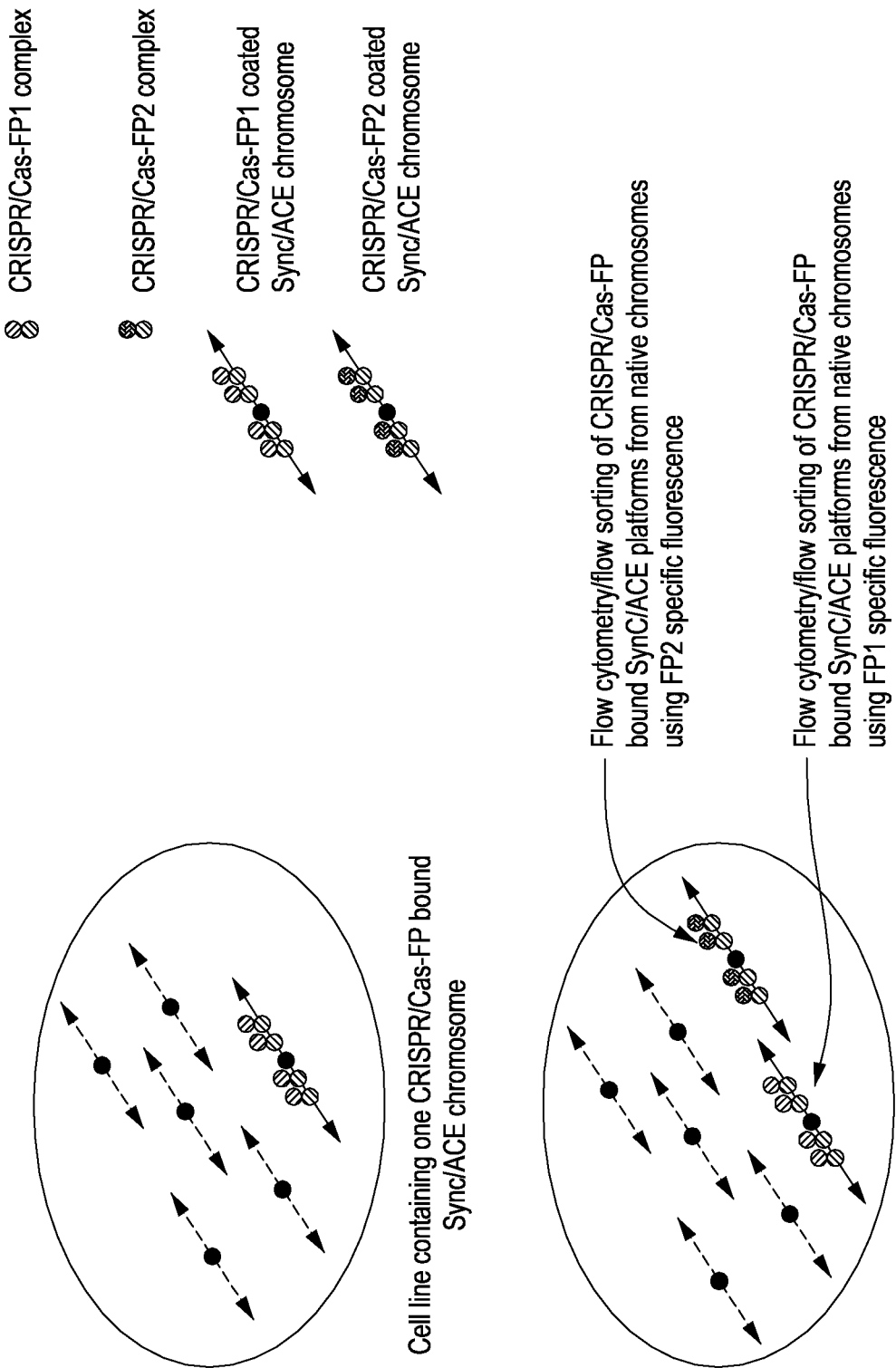
FIG. 9 is a graphic representation of using two different CRISPR/Cas fluorescent visualization systems for monitoring, isolating, and/or purifying a synthetic chromosome.
Figure 10:
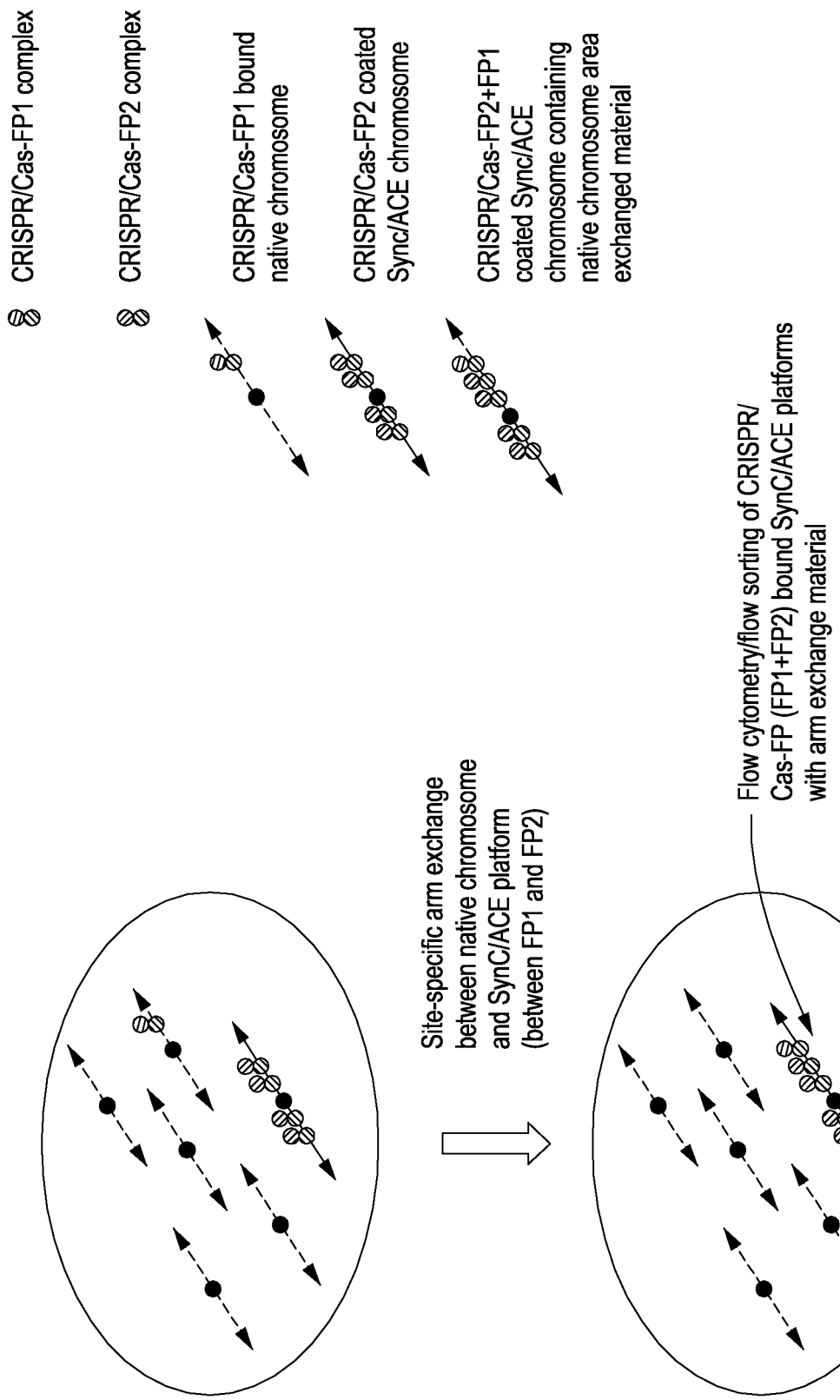
FIG. 10 is a graphic representation of using two different CRISPR/Cas fluorescent visualization systems for monitoring a chromosome arm exchange between an endogenous chromosome and a synthetic chromosome.

As discussed, above, in the discussion of FIGS. 1-4, the present invention is directed to two tags: one labeled tag specific to endogenous chromosomes in the synthetic chromosome production cell line, and one differently-labeled tag specific to a sequence on the synthetic chromosome that is to be produced. However, in yet other embodiments, additional tags could be implemented to distinguish multiple regions of the synthetic chromosome. The labeled tag specific to the endogenous chromosomes in the synthetic chromosome production reporter cell line is preferably a tag that is specific to all endogenous chromosomes in the cell line, such as, e.g., a histone-specific marker, such as a marker specific to histones H1, H2A, H2B, H3, H4, and H5. Alternatively, it is also contemplated that a collection of tags specific to different chromosomes, all linked to a single label (e.g., fluorescent protein) could be used. In preferred embodiments, the labeled tag specific to the endogenous chromosomes is a fusion peptide; however, the labeled tag specific to the endogenous chromosomes could also be a nucleic acid/protein chimera, with the tag portion being a nucleic acid sequence specific to the endogenous chromosomes and the label portion being a protein, such as a fluorescent or phosphorescent protein, or the tag portion could be a TALEN protein specific to the endogenous chromosomes with the label portion being a protein, such as a fluorescent, phosphorescent, or luminescent protein. Additionally, the tag portion could also be a modified CRISPR moiety (nuclease deficient) fused with a fluorescent protein and co-expressing a RNA moiety leading to specific binding and visualization of the synthetic chromosome (see, e.g., Chen et al., Cell, 155:1479-1491 (2013); and Chen and Huang, Methods in Enzymology, 546:337-354 (2014)). FIGS. 8-10 are graphic representations of using a CRISPR/Cas fluorescent visualization system for monitoring, isolating, and/or purifying a synthetic chromosome. In FIG. 8, a single reporter system is used, where the CRISPR moiety is fused with a fluorescent protein and a co-expressed RNA moiety leads to specific binding and visualization of the synthetic chromosome. FIG. 9 shows two different cell lines. One cell line contains one CRISPR/Cas/fluorescent moiety bound to a synthetic chromosome, and the other cell line shows two CRISPR/Cas/fluorescent moieties—one with fluorescent protein 1, the other with fluorescent protein 2-bound to two synthetic chromosomes. FIG. 10 shows the use of two different CRISPR/Cas/fluorescent moieties to detect site-specific arm exchange between a chromosome endogenous or native to the synthetic chromosome producing cells and a synthetic chromosome. The two different CRISPR/Cas/fluorescent moieties also allow the synthetic chromosome to be isolated.

Also, in preferred embodiments a labeled tag is chosen that is specific to and will mark all endogenous chromosomes; however, as mentioned it should be clear to those of ordinary skill in the art that more than one labeled tag could be employed, such as a plurality of labeled tags specific to a single or small number of chromosomes or a plurality of tags each specific to a single chromosome.

In preferred embodiments, the tag specific to the synthetic chromosome comprises a nucleic acid sequence complementary to an unique nucleic acid sequence on the synthetic chromosome such as any list of $4^n$ nucleotides—which has a high probability of being unique and can be screened against the database of known sequences—and a fluorescent protein as a nucleic acid/protein chimera. In preferred embodiments, the synthetic chromosome-specific tag is specific to site-specific integration sequences (acceptor sites) on the synthetic chromosome; thus, the signal from the labeled tag indirectly acts as a measure of the number of acceptor sites and the produced synthetic chromosomes can be sorted by their number of acceptor sites.

The labels contemplated for use in the present invention include any visible labels that can be utilized in conjunction with the tag specific to endogenous chromosomes in the synthetic chromosome production cell line, and the tag specific to a sequence on the synthetic chromosome. In preferred embodiments, the labels are fluorescent labels that are transcribed and translated by the synthetic chromosome production cell into a fusion protein or nucleic acid/protein chimera incorporating the tags. Fluorescent proteins of particular use in the invention include but are not limited to TagBFP, TagCFP, TagGFP2, TagYFP, TagRFP, FusionRed, mKate2, TurboGFP, TurboYFP, TurboRFP, TurboFP602, TurboFP635, or TurboFP650 (all available from Evrogen, Moscow); AmCyan1, AcvGFP1, ZsGreen1, ZsYellow1, mBanana, mOrange, mOrange2, DsRed-Express2, DsRed-Express, tdTomato, DsRed-Monomer, DsRed2, AsRed2, mStrawberry, mCherry, HcRed1, mRaspberry, E2-Crimson, mPlum, Dendra 2, Timer, and PAmCherry (all available from Clontech, Palo Alto, Calif.); HALO-tags; infrared (far red shifted) tags (available from Promega, Madison, Wis.); and other fluorescent tags known in the art, as well as fluorescent tags subsequently discovered.

Visualization and Monitoring

If the reporter tags of the present invention are labeled with fluorescent labels, localization of the labels in the synthetic chromosome production cells may be accomplished with fluorescent microscopy. Generally, the cells are excited with a light source at the excitation wavelength of the particular fluorescent labels being used and the resulting fluorescence at the emission wavelength is detected. In a preferred embodiment, the excitation light source is a laser appropriate for the excitation of the fluorescent label. A confocal microscope used to detect the labels may be automated with a computer-controlled stage to automatically scan the entire cell culture dish. Similarly, the microscope may be equipped with a phototransducer (e.g., a photomultiplier, a solid state array, a CCD camera, etc.) attached to an automated data acquisition system to automatically record the fluorescence signal produced by each cell or cell colony in culture. Alternatively, one may also employ imaging flow cytometers that captures an image of each "cell" in the flow stream following laser excitation, such as Flowsight (Amnis, Seattle, Wash.); thus automating the assessment of each cell colony for production of a synthetic chromosome.

Figure 7:
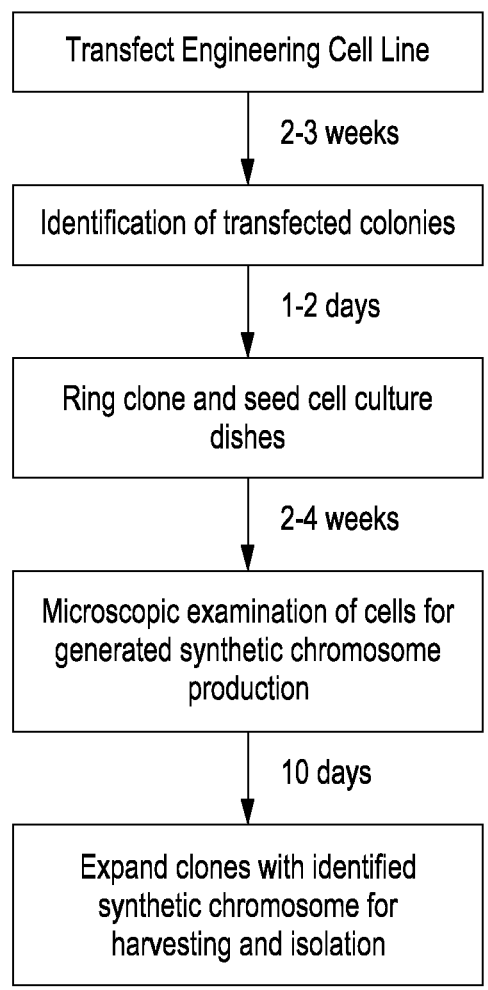
FIG. 7 shows a timeline of real-time synthetic chromosome production using the methods of the present invention.

Lindenbaum and Perkins, et al., Nucleic Acid Research, 32(21):e172 (2004) describe the production of a mammalian satellite DNA-based Artificial Chromosome Expression (ACE) System using prior art technology. In this prior art system, conventional single-color and two-color FISH analysis and high-resolution FISH were carried out using PCR-generated probes or using nick-translated probes. For detection of telomere sequences, mitotic spreads were hybridized with a commercially-obtained peptide nucleic acid probe. Microscopy was performed using fluorescent microscopy. The process took approximately three months. The present invention allows for one to decrease or entirely eliminate repeated FISH analysis, eliminates the need for potentially mutagenic dyes that would be used to sort the chromosome by the new method in this application, and allows one to watch the development of the synthetic chromosome in real time. In addition, the methods of the present invention allow for easier downstream engineering of the synthetic chromosome where DNA elements of interest inserted into the synthetic chromosome. FIG. 7 shows a timeline for the methods of producing synthetic chromosomes as described herein.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

Construction of Vectors to Deliver Tags

For the real-time monitoring of the synthetic platform chromosome, the cell line HT1080 was engineered to carry an endogenous chromosome-specific tag vector—a tag that identifies all native, endogenous chromosomes, along with a synthetic chromosome-specific tag vector—a tag that identifies the synthetic chromosome apart from the endogenous chromosomes (see FIG. 6, and see, e.g., Robinett, et al., J Cell Biol., 135(6 Pt 2):1685-700 (1996)). The endogenous chromosome-specific tag comprised a chromosome-specific binding moiety, e.g., a DNA binding protein such as a histone protein (see, e.g., Kimura, et al., J Cell Biol., 153(7):1341-53 (2000)), proteins involved in chromatin structure, or a genome editing protein such as zinc finger nuclease (ZFN), transcription activator-like effector nuclease (TALEN) (see, e.g., Thanisch, et al., Nucleic Acids Res., 42(6):e38 (2014); and Miyanari, et al., Nat Struct Mol Biol., 20(11):1321-24 (2013)), CRISPER/Cas system proteins (see, e.g., Anton, et al., Nucleus, 5(2):163-72 (2014)), or an engineered meganuclease. For the endogenous chromosome-specific tag, the chromosome specific binding moiety was fused and expressed along with a reporter moiety that was detected by standard microscopic or flow cytometry methodology. The reporter moiety comprises in preferred embodiments molecules such as fluorescent molecules (e.g., green fluorescent protein) or protein fusion tags bonded to chemical ligands (e.g., HaloTags).

The synthetic chromosome-specific tag vector comprised a DNA sequence specific binding moiety, such as, for example, a bacterial Lac repressor protein that binds to Lac operon sequences engineered onto the synthetic chromosome or genome editing proteins (e.g., TALENS, RNA/CRISPR-CAS) engineered to bind to DNA sequences specific to the synthetic chromosome. The synthetic chromosome-specific tag was fused and expressed along with a reporter moiety that can be detected by standard microscopic or flow cytometry methodology. The reporter moiety fused to the synthetic chromosome-specific tag comprises in preferred embodiments molecules such as fluorescent molecules (e.g., red fluorescent protein) or protein fusion tags bonded to chemical ligands (e.g., HaloTags).

The endogenous chromosome-specific tag and the synthetic chromosome-specific tag were expressed from promoters (e.g., the human glucose-6-phosphate isomerase promoter) and expressed from two unique vectors though the endogenous chromosome-specific tag and the synthetic chromosome-specific tag could be combined onto a single vector with amenable drug selection (e.g., an expressed gene conferring hygromycin resistance) (again, see FIG. 5). Alternatively, the endogenous chromosome-specific tag and synthetic chromosome-specific tag can be expressed from an inducible promoter (e.g., the tetracycline regulable promoter). For subsequent removal of tags and/or tag vector sequences from the engineering cell line, site-specific recombination sequences (e.g., loxP sequences) were placed onto and flanking the endogenous chromosome-specific tag vector and the synthetic chromosome-specific tag vector, and these sequences were selectively eliminated by introducing the appropriate site-specific recombinase (e.g., Cre protein) and identifying the resulting recombinants by standard microscopic or flow cytometry methodology.

Example 2

Delivery of Tag Vectors into Host Cell Line Genome

For transfection of the tag vectors into the host cell line genome, linearized tag vector DNA was introduced into the HT1080 host cell genome using standard mammalian cell transfection reagents including but not limited to lipofectamine LTX (ThermoFisher) or Viafect (Promega) and allowed to grow in culture approximately 2-5 days. Upon integration into the host cell genome, expression from the integrated endogenous chromosome specific and synthetic chromosome specific tags allowed for FACs selection of host cells producing both tags.

The day before transfection, the HT1080 host cell line cells were split to a density of approximately $2-8\times10^4$ adherent cells into each well of a 24-well tissue culture dish, and the tag-element vectors, such as pMC1, were purified (e.g., using a Qiagen EndoFree Plasmid Maxi Kit, Qiagen, Valencia, Calif.), linearized, and the concentration of the vectors was determined for transfection. The cultured HT1080 cells were fed 3-5 hours before transfection. The pMC1 vector comprises the EF1/HTLV promoter, the green fluorescent protein marker sequence, the lac IF; the SV40 poly A, an IFN-beta scaffold/matrix attachment region, the R6K origin of replication, a beta glow matrix attachment region, a histone H2B sequence, the mCherry selection marker, an IRES sequence, a hygromycin resistance gene, a bGH polyA and 3' UTR sequence. 250-500 ng of vector DNA per well of a 24-well semiconfluent tissue culture dish was used to transfect the HT1080 cells using, e.g., Lipofectamine-LTX mediated transfection (Life Technologies, Inc., Grand Island, N.Y.). Cells were maintained for 1-5 days post-transfection at which point they were trypsinized and transferred to 10 cm dishes. Hygromycin selection medium was added to the 10 cm dish at the time of plating to the 10 cm dish or 1-3 days after plating. Hygromycin resistant clones were ring-cloned and expanded in 24-well dishes. Clones expressing both tag-elements were single-cell sorted into 96-well tissue culture dishes. Single-cell clones were expanded in culture and monitored using a fluorescence microscope as they grew in culture to identify clones with optimal performance of the integrated tag-elements. Optimal candidates were expanded in culture and placed in cold storage by standard methods for future use.

Example 3

De Novo Generation of Satellite DNA-Based Artificial Chromosome

For de novo production of synthetic chromosomes, exogenous DNA sequences were introduced into HT1080 synthetic chromosome production cell line, and, upon integration into the pericentric heterochromatic regions of acrocentric chromosomes, a large-scale amplification of the short arms of the acrocentric chromosome (rDNA/centromere region) was triggered. During the amplification event, the centromere was duplicated resulting in a dicentric chromosome with two active centromeres. Subsequent mitotic events resulted in cleavage and resolution of the dicentric chromosome, leading to a breakoff of approximately 20-120 Mb in size comprised predominantly of satellite repeat sequences with subdomains of coamplified transfected transgene that may also contain amplified copies of rDNA. The newly generated synthetic chromosome is validated by observation of fluorescent chromosome painting, via the endogenous chromosome tag and synthetic chromosome tag that has been engineered into the HT1080 synthetic chromosome production cell line.

The day before transfection, the HT1080 synthetic chromosome production cell line cells were split to a density of approximately 2.0 to $8.0\times10^4$ adherent cells into 24-well tissue culture dishes, and the vectors comprising the exogenous DNA were purified (e.g., using a Qiagen EndoFree Plasmid Maxi Kit), linearized, and the concentration of the vectors was determined for transfection. The cultured HT1080 cells were fed 3-5 hours before transfection. 225 ng of pSPOP48lacHurDNA vector and 12.5 ng EF1alphaattPPuro vector per 24-well semiconfluent tissue culture dish was used to transfect the HT1080 cells using standard transfection reagents, e.g., ThermoFisher Lipofectamine LTX, Promega's Viafect, or Invitrogen's Calcium Phosphate Transfection Kit. The pSPOP48lacHurDNA vector comprises the LacI repeats and ribosomal DNA sequences. The EF1alphaattPPuro vector comprises the components for the site-specific recombination system and an ampicillin and a puromycin resistance gene. Cells were maintained for 1-3 days post-transfection at which point they were trypsinized and replated onto a 10 cm dish. Selective medium was added to the 10 cm dish at the time of plating or 1-3 days post plating. Selective conditions were maintained for 10-21 days with media changed every 2-3 days. Antibiotic resistant clones were picked when a colony reached 2-3 mm in diameter. Colonies that were well separated are preferred. Cells were removed by use of a cloning cylinder and trypsin, and transferred to a 24-well plate for expansion.

Example 4

Real-time Monitoring of Synthetic Chromosome Platform

For the creation of synthetic chromosome platforms, the HT1080 synthetic chromosome production reporter cells expressing the endogenous chromosome-specific tag, e.g., a human H2B—RFP fusion protein, and the synthetic chromosome-specific tag, e.g., a Lac repressor fused to GFP, LacI-GFP are seeded approximately 2.0 to $8\times10^4$ adherent cells into 24-well tissue culture dishes. The chromosome-specific tag proteins are constitutively expressed. One day after seeding, transfection is carried out using standard transfection methodology such as Invitrogen's Calcium Phosphate Transfection Kit, Lipofectamine-LTX mediated transfection (Life Technologies, Inc., Grand Island, N.Y.) or Viafect (Promega). For the transfection into the HT1080 engineering cell line, a linearized vector (pSPOP48lacHurDNA) is co-transfected along with a linearized plasmid (pEF1alphaattPPuro) carrying a site-specific recombination site (e.g., attP) inserted between a human promoter and a drug selectable marker (e.g., Puromycin resistance). In addition, pSPOP48lacHurDNA contains approximately 48 copies of the synthetic chromosome-specific tag recognition sequence (e.g., 48 copies of the lac operator sequences, lacO); the sequence that is recognized and bound by the synthetic chromosome-specific tag LacI-GFP. For co-transfections, excess pSPOP48lacHurDNA is delivered along with the pEF1alphaattPPuro plasmid (>3:1 molar excess of pSPOP48lacHurDNA to pEF1alphaattPPuro). Twenty-four hours post transfection, the HT1080 cells from each well of the 24-well dish are trypsinized and plated to a 10 cm cell culture dish (one well of a 24-well dish into one 10 cm dish) and incubated. One to four days post transection, the culture medium is replaced with selection medium consisting of complete medium containing 0.5 micrograms/ml puromycin. Selection medium is changed three times per week for 2-3 weeks until the appearance of drug resistant clones are visible by eye. Note that if upon initial fluorescence microscopic examination of candidates in 24-well dishes, clones with mature synthetic chromosome break-off products are observed, the examination of cells by fluorescence microscopy can be shifted earlier to observations in the 10 cm tissue culture dishes prior to ring cloning. As the process of generating synthetic chromosomes has been blind in the past, the time for initial synthetic chromosome formation is not fully determined.

When clones are visible, 96 clones are isolated by ring cloning and each clone is transferred into a well of a 24-well tissue culture dish and cultured with drug selection. At this time cells near confluence in the 24-well dish (2-10 days) are harvested using trypsin treatment and each clonal cell suspension is distributed between equivalent wells on two separate 24-well plates. One dish is used for real-time monitoring of synthetic chromosome production while the other equivalent dish is used for routine maintenance and growth. During growth in the 24-well dishes that are monitored for synthetic chromosome production, cells are analyzed every 48 hours utilizing standard fluorescence microscopy and checked for the appearance of mitotic cells that exhibit red labelled endogenous chromosomes (presence of the H2B—RFP binding to the endogenous chromosomes) and co-localized, punctate staining of the synthetic chromosome tag; that is, presence of the LacI-GFP tag on newly synthesized platform chromosomes or "sausage" chromosomes, the precursor of synthesized platform chromosomes. Targeting of the pSPOP48lacHurDNA and pEF1alphaattPPuro vectors into the centromeric/rDNA regions of native acrocentric chromosomes induces intrinsic, large scale amplification of the integrated plasmids, including expansion of the lacO repeated array, and the formation of dicentric chromosomes with subsequent break-off and synthetic chromosome production. If needed, cell cycle arresting agents such as colcemid (KaryoMax colcemid solution, Life Technologies, Inc., Grand Island, N.Y.) can be added to increase the population of cells in G2/M phase to facilitate the visible inspection of condensed chromosomes in real-time. The monitoring in real-time of synthetic chromosome production utilizing the endogenous chromosome tag and the synthetic chromosome tag alleviates the need for monitoring production using static methods such as fluorescent in situ hybridization (FISH). When cells from the 24-well dishes used for routine maintenance and growth reach near confluence, these cells are continually passaged into two separate 24-well dishes with one dish for further growth and maintenance and the other used for real-time monitoring until clones containing newly produced, mitotically stable synthetic chromosomes are identified—approximately 2-4 weeks. Microscopic photographs and or movies are taken of the cultures throughout the process to document the progression of the synthetic chromosome formation, i.e., integration of exogenous DNA elements; amplification of chromosomal regions with incorporated exogenous DNA; formation of a dicentric chromosome; and mitotic breakage of the dicentric chromosome.

Isolated clones that contain new synthetic chromosomes can be further expanded into three, 15 cm dishes. One dish is dedicated for long-term cryogenic storage. The remaining two dishes are arrested in metaphase using colcemid and synthetic chromosomes are harvested and purified as previously described (see, e.g., Vanderbyl et al., Cytometry, 44(2):100-05 (2001); and Lindenbaum and Perkins, et al., Nucleic Acid Res., 32(21):e172 (2004)). In contrast to the previously described methods that utilize potential mutagenic agents for counterstaining chromosomes (e.g., Hoechst and chromomycin A3), the binding and presence of the H2B—RFP and LacI-GFP on the synthetic platform chromosome permit dual color, fluorescent activated sorting and isolation of the synthetic chromosome for subsequent delivery into cells of therapeutic interest. Furthermore, isolated synthetic chromosomes coated with H2B—RFP and LacI-GFP can subsequently be utilized for assessing and optimizing delivery of the synthetic chromosomes into cell types of interest, that is, monitoring the percentage of transfected cells that have delivered synthetic chromosomes by fluorescence. An overview of this process is shown in FIG. 7.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. § 112, ¶6.

We claim:

1. A method for screening production of synthetic chromosomes in living eukaryotic host cells, using a real-time tracking system having at least two tags, the method comprising:
    transfecting real-time tracking system components into a synthetic chromosome production eukaryotic host cell line, wherein the tracking system components comprise:
        (i) an endogenous chromosome tag that labels one or more endogenous chromosomes in the chromosome production host cell line;
        (ii) a differently-labeled synthetic chromosome-specific tag that identifies, apart from the endogenous chromosomes, a synthetic chromosome as it is being produced; and
    monitoring the production of the synthetic chromosome in the living synthetic chromosome production eukaryotic host cells in real-time by detecting the endogenous chromosome tag and the synthetic chromosome tag.

2. The method of claim 1, wherein the endogenous chromosome tag and the synthetic chromosome-specific tag are stably integrated into the synthetic chromosome production host cell line's genome.

3. The method of claim 1, wherein the endogenous chromosome tag becomes stably integrated into the synthetic chromosome production host cell line's genome and the synthetic chromosome-specific tag becomes stably integrated into the synthetic chromosome.

4. The method of claim 1, wherein the endogenous chromosome tag and the synthetic chromosome-specific tag are stably integrated into the synthetic chromosome.

5. The method of claim 1, wherein the endogenous chromosome tag becomes stably integrated into the synthetic chromosome and the synthetic chromosome-specific tag becomes stably integrated into the synthetic chromosome production host cell line's genome.

6. The method of claim 1, wherein an arm of an endogenous chromosome present in the synthetic chromosome production host cell line comprises a recombination site compatible for interaction with a recombination site in the synthetic chromosome.

7. The method of claim 1, wherein the endogenous chromosome tag and the synthetic chromosome-specific tag comprise fluorescent tags, and the monitoring step is performed by fluorescence microscopy.

8. The method of claim 7, wherein the fluorescent tags are selected from TagBFP, TagCFP, TagGFP2, TagYFP, TagRFP, FusionRed, mKate2, TurboGFP, TurboYFP, TurboRFP, TurboFP602, TurboFP635, TurboFP650, AmCyan1, AcvGFP1, ZsGreen1, ZsYellow1, mBanana, mOrange, mOrange2, DsRed-Express2, DsRed-Express, tdTomato, DsRed-Monomer, DsRed2, AsRed2, mStrawberry, mCherry, HcRed1, mRaspberry, E2-Crimson, mPlum, Dendra 2, Timer, PAmCherry, HALO-tags, and infrared-shifted fluorescent proteins.

9. The method of claim 1, wherein the tags of the endogenous chromosome tag and the synthetic chromosome-specific tag comprise:
    (i) chemiluminescent tags and the monitoring step is performed by chemiluminescent microscopy, or
    (ii) phosphorescent tags and the monitoring step is performed by phosphorescent microscopy.

10. The method of claim 1, wherein the endogenous chromosome tag comprises a marker specific to histones H1, H2A, H2B, H3, H4, or H5.

11. The method of claim 1, wherein the synthetic chromosome-specific tag comprises $4^n$ nucleotides that have been screened against a database of known sequences.

12. The method of claim 1, wherein the synthetic chromosome production eukaryotic host cell line is selected from an animal cell line, a plant cell line, a mammalian cell line, a rodent cell line, a zebrafish cell line, an embryonic cell line, a pluripotent cell line, an adult-derived stem cell, a reprogrammed cell line and a human cell line.

13. The method of claim 12, wherein the synthetic chromosome production host cell line is human cell line HT1080.

14. The method of claim 1, wherein the synthetic chromosome production host cell line is transfected with tracking system components to produce synthetic chromosomes via a top down approach.

15. The method of claim 1, wherein the synthetic chromosome production host cell line is transfected with tracking system components to produce synthetic chromosomes via a bottom up approach.

16. The method of claim 1, wherein the synthetic chromosome production host cell line is transfected with tracking system components to produce synthetic chromosomes via engineering of naturally occurring minichromosomes.

17. The method of claim 1, wherein the synthetic chromosome production host cell line is transfected with tracking system components to produce synthetic chromosomes via de novo chromosome generation by targeted amplification of chromosomal segments.

18. The method of claim 17, wherein the chromosomal segments are pericentric regions of a chromosome.

19. The method of claim 1, wherein the endogenous chromosome tag comprises a plurality of endogenous chromosome tags.

20. The method of claim 1, wherein the endogenous chromosome tag is a fusion protein, nucleic acid/protein chimera, nucleic acid/protein complex, a RNA/CRISPR-CAS9 complex, or a moiety comprising a TALEN protein specific to the endogenous chromosomes and a fluorescent or phosphorescent label.

21. The method of claim 1, wherein the tracking system components further comprise one or more of: an endogenous chromosome binding moiety; a first reporter moiety; a second reporter moiety; a synthetic chromosome binding moiety; and a selectable marker.

* * * * *